US008465765B2

(12) United States Patent
Mehta et al.

(10) Patent No.: US 8,465,765 B2
(45) Date of Patent: *Jun. 18, 2013

(54) ORALLY EFFECTIVE METHYLPHENIDATE EXTENDED RELEASE POWDER AND AQUEOUS SUSPENSION PRODUCT

(75) Inventors: Ketan Mehta, Cranbury, NJ (US); Yu-Hsing Tu, West Windsor, NJ (US); Ashok Perumal, Edison, NJ (US)

(73) Assignee: Tris Pharma, Inc., Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,183

(22) Filed: Sep. 12, 2012

(65) Prior Publication Data
US 2013/0004571 A1 Jan. 3, 2013

Related U.S. Application Data

(63) Continuation of application No. 13/244,706, filed on Sep. 26, 2011, now Pat. No. 8,287,903, which is a continuation of application No. PCT/US2011/024873, filed on Feb. 15, 2011.

(51) Int. Cl.
*A61K 9/48* (2006.01)

(52) U.S. Cl.
USPC .......................................... 424/452

(58) Field of Classification Search
None
See application file for complete search history.

(56) References Cited

U.S. PATENT DOCUMENTS

| 2,507,631 | A | 5/1950 | Hartmann | |
|---|---|---|---|---|
| 2,957,880 | A | 10/1960 | Rudolf | |
| 4,221,778 | A | 9/1980 | Raghunathan | |
| 4,459,278 | A | 7/1984 | Porter | |
| 4,876,094 | A | 10/1989 | Benton | |
| 5,275,820 | A * | 1/1994 | Chang | 424/426 |
| 5,837,284 | A | 11/1998 | Mehta | |
| 5,874,090 | A | 2/1999 | Baker | |
| 5,908,850 | A | 6/1999 | Zeitlin | |
| 6,001,392 | A | 12/1999 | Wen | |
| 6,046,277 | A | 4/2000 | Kolter | |
| 6,066,334 | A | 5/2000 | Kolter | |
| 6,217,904 | B1 * | 4/2001 | Midha et al. | 424/468 |
| 6,228,398 | B1 | 5/2001 | Devane | |
| 6,231,936 | B1 | 5/2001 | Kozimor | |
| 6,344,215 | B1 * | 2/2002 | Bettman et al. | 424/459 |
| 6,355,656 | B1 | 3/2002 | Zeitlin | |
| 6,432,440 | B1 | 8/2002 | Watts | |
| 6,528,530 | B2 | 3/2003 | Zeitlin | |
| 6,551,630 | B2 | 4/2003 | Otterbeck | |
| 6,555,136 | B2 * | 4/2003 | Midha | 424/469 |
| 6,635,284 | B2 | 10/2003 | Mehta | |
| 6,667,058 | B1 | 12/2003 | Goede | |
| 6,673,367 | B1 | 1/2004 | Goldenheim | |
| 6,730,325 | B2 | 5/2004 | Devane | |
| 6,919,373 | B1 | 7/2005 | Lam | |
| 7,067,116 | B1 | 6/2006 | Bess | |
| 7,083,808 | B2 * | 8/2006 | Goldenheim et al. | 424/490 |
| 7,115,631 | B2 | 10/2006 | Zeitlin et al. | |
| 7,691,880 | B2 | 4/2010 | Herman | |
| 7,906,145 | B2 * | 3/2011 | Castan et al. | 424/489 |
| 8,062,667 | B2 * | 11/2011 | Mehta et al. | 424/484 |
| 8,202,537 | B2 | 6/2012 | Mehta et al. | |
| 8,287,903 | B2 | 10/2012 | Mehta et al. | |
| 2002/0156133 | A1 | 10/2002 | Bartholomaeus | |
| 2003/0099711 | A1 * | 5/2003 | Meadows et al. | 424/474 |
| 2004/0096501 | A1 | 5/2004 | Vaya | |
| 2004/0228830 | A1 * | 11/2004 | Hirsh et al. | 424/78.12 |
| 2005/0181050 | A1 * | 8/2005 | Hirsh et al. | 424/469 |
| 2005/0232986 | A1 | 10/2005 | Brown | |
| 2005/0232987 | A1 | 10/2005 | Srinivasan | |
| 2005/0232993 | A1 | 10/2005 | Brown | |
| 2006/0018933 | A1 | 1/2006 | Vaya | |
| 2006/0018934 | A1 | 1/2006 | Vaya | |
| 2006/0115529 | A1 | 6/2006 | Jeong | |
| 2006/0134148 | A1 * | 6/2006 | Hollenbeck | 424/400 |

(Continued)

FOREIGN PATENT DOCUMENTS

WO WO 98/27961 A2 7/1998
WO WO 00/40224 A1 7/2000

(Continued)

OTHER PUBLICATIONS

Response and Amendment dated Jul. 23, 2012 filed in U.S. Appl. No. 13/244,706.
Aoyama, T., et al., "Pharmacodynamic Modeling for Change of Locomotor Activity by Methylphenidate in Rats", 1997, Pharmaceutical Research, vol. 14, No. 11, pp. 1601-1606.
BASF, Product Catalog, 2008.
Childress, AC, et al., "The Single-Dose Pharmacokinetics of NWP06, a Novel Extended-Release Methylphenidate Oral Suspension", Postgraduate Medicine, vol. 122, Issue 5, Sep. 2010, pp. 35-41.
Dashevsky A., et al, "Compression of pellets coated with various aqueous polymer dispersions", Intl J Pharm, 279, pp. 19-26, avail on-line (Jun. 7, 2004).
Jeong, SH, "Development of Sustained Release Fast-melting Tablets Using Ion Exchange Resin Complexes", (accepted Nov. 29, 2005), Dissertations Submitted to Purdue University, W. Lafayette, Indiana, UMI #3210729.

(Continued)

*Primary Examiner* — Robert A Wax
*Assistant Examiner* — Olga V Tcherkasskaya
(74) *Attorney, Agent, or Firm* — Cathy A. Kodroff; Howson & Howson LLP; Egon Berg

(57) ABSTRACT

An oral methylphenidate powder which is reconstitutable into a final oral aqueous sustained release formulation containing at least about 50%, or at least about 80% by weight water based on the total weight of the suspension, is provided. The powder is a blend containing a combination of an uncoated methylphenidate-ion exchange resin complex, a barrier coated methylphenidate-ion exchange resin complex-matrix, and a water soluble buffering agent such that upon formed into an aqueous liquid formulation, the formulation has a pH in the range of about 3.5 to about 5, or about 4 to about 4.5. Following administration of a single dose of the oral aqueous methylphenidate suspension, a therapeutically effective amount of methylphenidate is reached in less than one hour and the composition provides a twelve-hour extended release profile.

30 Claims, 5 Drawing Sheets

U.S. PATENT DOCUMENTS

| | | | |
|---|---|---|---|
| 2006/0135777 A1 | 6/2006 | Trafelet | |
| 2006/0240105 A1* | 10/2006 | Devane et al. | 424/470 |
| 2006/0240128 A1* | 10/2006 | Schlagheck | 424/725.1 |
| 2007/0160675 A1* | 7/2007 | Devane et al. | 424/489 |
| 2007/0215511 A1 | 9/2007 | Mehta et al. | |
| 2008/0069870 A1* | 3/2008 | Jenkins et al. | 424/456 |
| 2008/0118570 A1 | 5/2008 | Liu et al. | |
| 2008/0118571 A1* | 5/2008 | Lee et al. | 424/494 |
| 2008/0124389 A1* | 5/2008 | Jenkins et al. | 424/455 |
| 2009/0011027 A1* | 1/2009 | Pathak et al. | 424/486 |
| 2010/0166858 A1 | 7/2010 | Mehta | |
| 2010/0260844 A1* | 10/2010 | Scicinski et al. | 424/484 |
| 2012/0015030 A1 | 1/2012 | Mehta et al. | |
| 2012/0135077 A1 | 5/2012 | Mehta et al. | |
| 2013/0004452 A1 | 1/2013 | Mehta et al. | |

FOREIGN PATENT DOCUMENTS

| | | |
|---|---|---|
| WO | WO 03-020242 | 3/2003 |
| WO | WO 2004/060357 A1 | 7/2004 |
| WO | WO 2004-067039 | 8/2004 |
| WO | WO 2005-117843 | 12/2005 |
| WO | WO 2006-101536 | 9/2006 |
| WO | WO-2007-109104 | 9/2007 |
| WO | WO-2010-080787 | 7/2010 |

OTHER PUBLICATIONS

Jeong, SH, "Evaluation of Drug Release Properties from Polymer Coated Drug/Ion Exchange Resin Complexes Using Mathematical Simulation and Their Application into Sustained Oral Drug Delivery", Department of Pharmaceutical Chemistry, University of Kansas, Abstract, (Jun. 16-18, 2005).

Markowitz, JS, et al, "Advances in the Pharmacotherapy of Attention-Deficit-Hyperactivity Disorder: Focus on Methylphenidate Fonnulations", Posted Oct. 23, 2003; Pharmacotherapy, 2003; 23(10).

Pearnchob, N., et al, "Coating with Extended Release", ExACT, No. 12, Jun. 2004, pp. 2-5.

Product Literature, Concerta®, (methylphenidate HC1) Extended-release Tablets, rev Nov. 2010.

Product Literature, Daytrana™ (methylphenidate transdermal system), revised Dec. 2009.

Quadir, Anisul, FDA Excipient Workshop, "Development of High Functionality Excipients for Immediate and Sustained Release Dosage Forms", (Sep. 20, 2004).

Shao, ZJ, "Drug Release from Kollicoat SR 30D-Coating Nonpareil Beads: Evaluation of Coating Level, Plasticizer Type, and Curing Condition", AAPS Pharm Sci Tech, 3(2), 2002: article 15 (http://www.aapspharmscitech.org).

Shao, ZJ, et al., "Effects of Formulation Variables and Post-Compression Curing on Drug Rlease from a New Sustained-Release Matrix Material: PolvinylacetatePovidone", PharmDevTech, 6(2) (2001), pp. 247-254.

Unpublished U.S. Appl. 12/261,349, Mehta et al, filed Oct. 30, 2008.

Unpublished U.S. Appl. No. 12/908,796, Mehta et al, filed Oct. 20, 2010.

Unpublished U.S. Appl. No. 13/244,748, Mehta, et al., filed Sep. 26, 2011.

International Search Report and the Written Opinion of the International Search Report of International Application No. PCT/US2011/024873.

Office Action, dated Dec. 7, 2011 in U.S. Appl. No. 13/244,706.

Office Action, dated Dec. 23, 2011 in U.S. Appl. No. 13/244,706.

Office Action, dated Jun. 15, 2012 in U.S. Appl. No. 13/244,706.

Response and Rule 132 Declaration dated Mar. 7, 2012, filed in response to NFOA dated Dec. 7, 2011 in U.S. Appl. No. 13/244,706.

Unpublished U.S. Appl. No. 13/666,424, Mehta et al, filed Nov. 1, 2012.

US 7,431,994, 10/2008, Mehta (withdrawn)

* cited by examiner

ORALLY EFFECTIVE METHYLPHENIDATE EXTENDED RELEASE POWDER AND AQUEOUS SUSPENSION PRODUCT

CROSS-REFERENCE TO RELATED APPLICATIONS

This application is a continuation of U.S. patent application Ser. No. 13/244,706, filed Sep. 26, 2011, which is a continuation of International Patent Application No. PCT/US11/24873, filed Feb. 15, 2011, now pending.

BACKGROUND OF THE INVENTION

Methylphenidate hydrochloride (HCl) and dexmethylphenidate hydrochloride both have the empirical formula $C_{14}H_{19}NO_2 \cdot HCl$. Methylphenidate HCl is a racemic mixture of d,l-threo-methyl α-phenyl-2-piperidineacetate hydrochloride. Several commercial products, including, e.g., Ritalin®, Daytrana™, and Metadate™ contain methylphenidate HCl as the active drug. Dexmethylphenidate is the d-threo-enantiomer of racemic methylphenidate hydrochloride [Focalin® product literature]. There are several commercial products which contain dexmethylphenidate as the active drug.

The use of the central nervous system stimulants methylphenidate and dexmethylphenidate for the treatment of such conditions as attention deficit disorder (ADD) and attention deficit hyperactivity disorder (ADHD) in adults and children has been described [see, Focalin®, Concerta®, Ritalin®, Daytrana™ and Metadate® product literature]. This drug may also be used to treat depression and cognitive impairment following Traumatic Brain Injury [See, product literature for methylphenidate hydrochloride tablet which is commercially available from Lake Erie Medical DBA Quality Care Products LLC, and product literature of the other drug products identified herein].

Solid dose extended release methylphenidate or dexmethylphenidate products are commercially available. These products include, e.g., Focalin® XR, Concerta®; Ritalin® LA, and Metadate®. However, to applicant's knowledge, there is no commercially available extended release liquid product containing a methylphenidate.

The methylphenidate based medications are predominantly prescribed for children, including children as young as 3 years old where they have difficulty swallowing the solid dosage forms. There remains a need for a stable, long-acting liquid methylphenidate product which can be conveniently delivered in an oral, titratable formulation.

SUMMARY OF THE INVENTION

The present invention provides a methylphenidate extended release powder which may be mixed with water to form an orally administrable extended release aqueous suspension. Also provided is the orally administrable methylphenidate extended release aqueous suspension which is stable at room temperature. Methods of treating patients in need thereof with these methylphenidate extended release suspensions are further provided by the invention.

As used herein "methylphenidate" includes the active ingredient which is either (i) racemic mixture of two optical isomers d-threo-methylphenidate and 1-threo-methylphenidate or (ii) the active isomer d-threo-methylphenidate (also known as dexmethylphenidate). For convenience, methylphenidate is abbreviated "MPH" herein. and when reference is made herein to methylphenidate or MPH, it will be understood that either the racemic mixture (typically 50/50 d- to 1-) or dexmethylphenidate is encompassed by this term. Where only the racemate or dexmethylphenidate is desired, reference will be specifically made to one or the other. Thus, for the formulations described herein, the methylphenidate may be independently selected from racemic methylphenidate (e.g., a 50/50 mixture of D-methylphenidate and L-methylphenidate), and dexmethylphenidate.

In one aspect, the invention provides a methylphenidate aqueous extended release suspension comprising at least 50% by weight water based on the total weight of the liquid component of the suspension, wherein extended release is as defined herein. In one embodiment, the suspension contains at least about 80% water by weight based on the total weight of the suspension. In one embodiment, the suspension has a pH of about 3.5 to about 5. In another embodiment, the suspension has a pH of about 4 to about 5, or about 4 to about 4.5, or about 4.2.

In one embodiment, a methylphenidate aqueous extended release oral suspension is characterized by providing a methylphenidate plasma profile of any of FIG. 1, 3 or 4 at a dose equivalent to 72 mg and 60 mg of racemic methylphenidate HCl, respectively. In one embodiment, the methylphenidate aqueous extended release oral suspension comprises an immediate release methylphenidate component and a sustained release methylphenidate component.

In another aspect, the invention provides a methylphenidate extended release powder blend formulation which is reconstitutable into an orally administered aqueous extended release suspension formulation. The extended release powder blend formulation comprises (i) an immediate release methylphenidate component, (ii) a sustained release barrier coated methylphenidate-ion exchange resin complex-matrix, and (iii) an optional water soluble buffering agent. Upon being prepared as (e.g., reconstituted) an orally administrable aqueous extended release suspension formulation, the suspension has a pH in the range from about 3.5 to about 5, or about 4 to about 5, or about 4 to about 4.5. In one embodiment, the immediate release methylphenidate component is an uncoated methylphenidate-ion exchange resin complex, optionally in combination with a matrix forming polymer. In another embodiment, the barrier coating is a cured water-permeable, high tensile strength, water insoluble, barrier coating comprising a polyvinylacetate polymer and a plasticizer.

Alternatively, the barrier coating is selected from an ethylcellulose barrier coating and/or a coating based on poly(ethylacrylate-co-methyl methacrylate-cotrimethyl-ammoniumethylmethacrylate chloride) polymer.

In a further embodiment, the invention provides an aqueous methylphenidate extended release suspension formulation having a pH in the range of about 3.5 to 5 and comprising methylphenidate extended release powder blend as described herein, the water-soluble buffering agent to provide the desired pH, and water. In one embodiment, at least about 80% of the liquid component of the suspension is water.

In one embodiment, the invention provides an oral aqueous methylphenidate extended release suspension formulation reconstituted from a methylphenidate extended release powder blend in a liquid suspension base comprising at least about 80% water. The methylphenidate extended release powder blend comprises a combination of (a) a sustained release, cured, barrier coated methylphenidate-ion exchange resin complex-matrix, wherein the barrier coating comprises polyvinylacetate and a plasticizer and (b) an immediate release uncoated methylphenidate-ion exchange resin matrix, wherein the complex of (a) and the matrix of (b) are granules having an average size range of about 100 microns to about 250 microns. Optionally, the extended release powder blend further comprises an optional diluent granule comprising a buffering agent such that upon being formed into an aqueous liquid suspension, the suspension has a pH in the range of about 4 to about 4.5.

In a further embodiment, the invention provides a method of treating patients with a disorder for which methylphenidate is regulatory approved by administering an oral aqueous methylphenidate extended release suspension formulation as described herein.

Still other aspects and advantages of the invention will be apparent from the following detailed description of the invention.

DETAILED DESCRIPTION OF THE INVENTION

Figure 1:
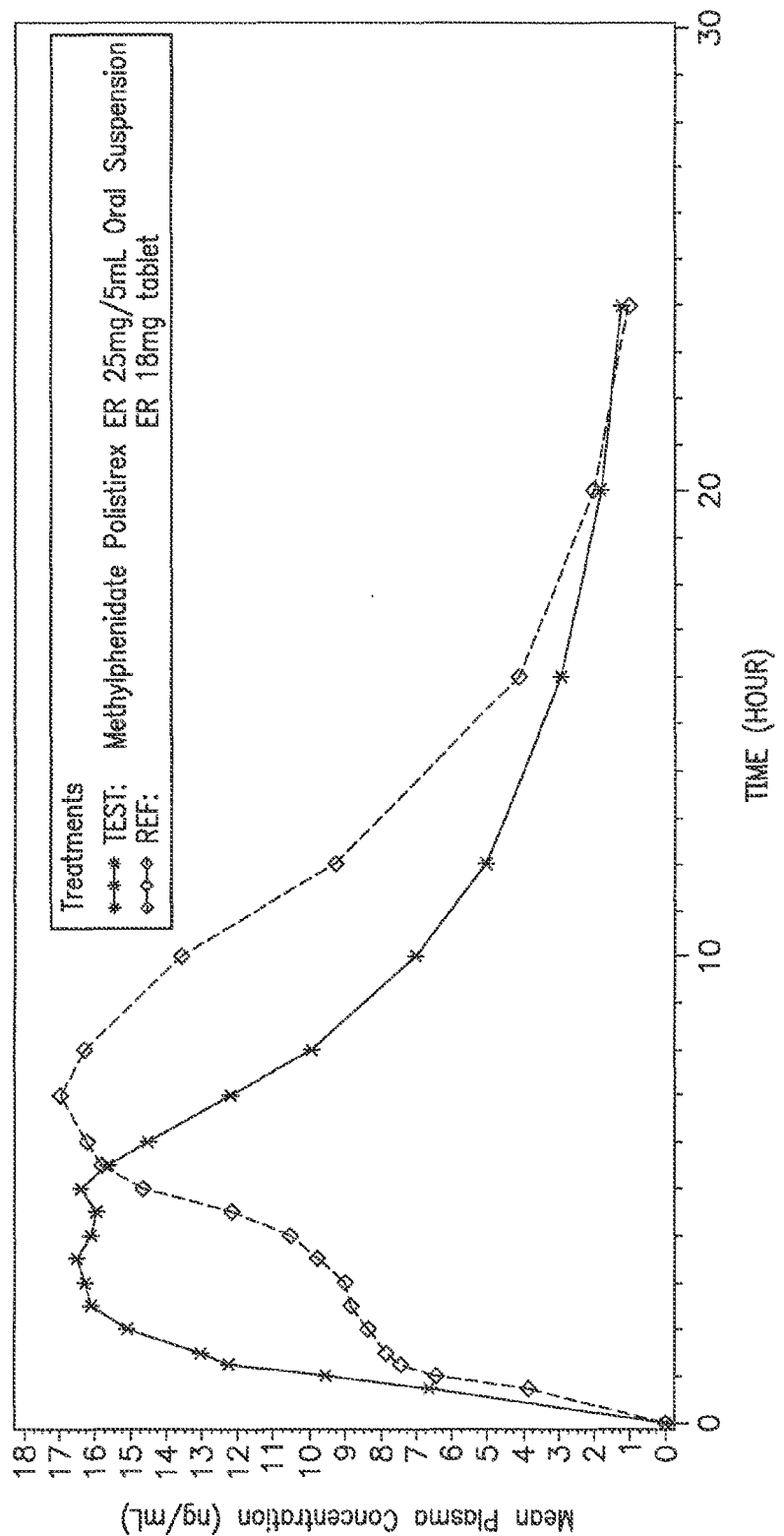
FIG. 1 is a linear plot of mean methylphenidate plasma concentration versus time. This study provides the pharmacokinetic (pK) profile of an oral aqueous extended release formulation of the invention containing the methylphenidate ER powder blend of Example 1 suspended in water to form an aqueous methylphenidate liquid suspension formulation having a concentration of 25 mg per 5 mL which formulation provides both an immediate release and an extended release profile. The oral aqueous liquid extended release formulation was dosed to provide an amount of methylphenidate equivalent to a 72 mg dose of methylphenidate HCl. A commercially available extended release methylphenidate HCl tablet (Concerta® solid formulation) was used for comparison.

In one aspect the invention provides a methylphenidate (MPH) extended release powder blend. The MPH extended release powder blend contains, at a minimum, a combination of an immediate release MPH component and a sustained release MPH component. While useful for formulation as a solid, the MPH extended release powder blend can readily be prepared as a suspension for oral delivery at the time the product needs to be used.

Suitably, following administration of a single dose of the oral MPH extended release suspension, in some embodiments, a therapeutically effective amount of MPH is reached as soon as about forty-five minutes and the formulation provides an extended release profile to at least about 12 hours.

As is often the case with psychoactive drugs, a therapeutic result for MPH is not solely related to plasma levels of the drug. Thus, "a therapeutically effective amount" of MPH includes the minimum amount of the drug required to provide a clinically observable psychological and/or behavioral response.

As used herein, the term "extended release" refers to compositions which are characterized by having at least one of the active components (i.e., methylphenidate or dexmethylphenidate) having a release over a period of at least about 12 hours. As with formulations described herein, "extended release" may be achieved by a single formulation containing both an "immediate release" component (release in less than 1 hour, e.g., as soon as about 45 minutes or as soon as about 30 minutes) and a "sustained release" (i.e., release for about 12 hours). The release profile may be assessed via in vitro dissolution using techniques known to those of skill in the art [e.g., USP basket method, Paddle Method, channel flow method, or other methods known in the literature]. The release profile can be assessed in vivo (e.g., for bioavailability determinations), using plasma concentrations to assess maximum plasma concentration ($C_{max}$) and area under the curve (AUC). Such assays are well known to those of skill in the art. [see, e.g., W. Wargin, et al., Pharmacokinetics of methylphenidate in man, rat and monkey. *J Pharmacol Exp Ther* August 1983 226:382-386].

"$C_{max}$" is the maximum observed plasma concentration, calculated as the mean of the individual maximum blood plasma concentrations.

The term "mean maximum plasma concentration" (mean $C_{max}$) is defined for the purposes of the present invention as the maximum mean plasma drug concentration.

"Mean plasma concentration" is the arithmetic mean blood plasma concentration.

The term "$T_{max}$" is the time at which the peak (maximum) observed blood plasma drug concentration for each individual participating in the bioavailability study.

The term "$AUC_0$-∞" or "$AUC_{inf}$" is the mean area under the plasma concentration-time curve extrapolated to infinity. It is calculated as the arithmetic mean of the area under the plasma concentration-time curve from time 0 extrapolated to infinity, calculated for each individual participating in the bioavailability study.

AUCpR is the area under the curve to the population median $T_{max}$ of the reference formulation. $AUC_{0-t}$ is the area under the plasma/serum/blood concentration-time curve from time zero to time t, where t is the last time point with measurable concentration for individual formulation.

T/R ratio refers to the test formulation (methylphenidate polistirex 25 mg/5 mL ER oral suspension) to reference (R) formulation.

Intra-subject CV % refers to the geometric (CV) coefficient of variation between subjects.

The term "half-life" is the apparent terminal elimination half-life ($T_{1/2}$).

The term "immediate release" is the release of an active ingredient (e.g., MPH) from a pharmaceutical formulation where the rate of release of the active pharmaceutical ingredient from the pharmaceutical formulation is not retarded by means of a controlled release matrix or other such means and where the components of the pharmaceutical formulation are designed such that, upon ingestion, maximum exposure of said active pharmaceutical ingredient to body tissues occurs in the minimum period of time. As described herein, an "immediate release" MPH component preferably releases in less than 1 hour, e.g., as soon as about 45 minutes or as soon as about 30 minutes. Further, in one embodiment, the MPH immediate release component releases at least about 50% of the MPH within about the first hour following administration, and at least about 80% of the MPH within about 90 minutes following administration. As will be seen from the following detailed description, a MPH-ion exchange resin complex, optionally in a matrix, and may provide the immediate release component.

The term "initial administration" is defined for purposes of the present invention as the first single dose of a formulation containing an active ingredient administered to a patient or subject or the first dose administered to a patient or subject after a suitable washout period.

As used herein, a therapeutically effective amount of MPH is at least the minimum amount of MPH which reduces or eliminates the symptoms associated with a condition for which MPH has been approved for use. Appropriate doses are discussed in more detail later in this specification.

The invention minimizes stability problems attributed to prior art liquid MPH formulations and permits the orally administrable MPH extended release suspension formulation to be primarily aqueous based. The aqueous liquid suspension of the invention is one in which water is greater than 50% by weight of the liquids in the suspension. In one embodiment, water is greater than about 60%, greater than about 70%, greater than about 80%, greater than about 90%, or up to 100% by weight of the liquid component of the suspension formulation.

In contrast to prior art formulations which have been reported as a mixture of primarily non-aqueous solvents in combination with water, requiring more than 50% non-aqueous solvents, the present invention is an aqueous liquid formulation. The formulations of the invention contain less than 10% non-aqueous solvents, and in certain embodiments, less than 5%, or less than 2% non-aqueous solvents. In further embodiments, the formulations of the invention may optionally also contain minimal amounts of components which are humectants, e.g., less than about 10%.

Additionally, the liquid suspension MPH extended release product makes it convenient for physicians to titrate the dose for patients to introduce the drug in incremental doses of medication or for patients who require incremental doses of medication so as to better tolerate the drug. This ability to titrate the dose allows physicians to take into consideration individual patient needs, including factors like age, body weight and individual response to the medication without the need for taking multiple doses of an immediate release product over a 12 hour period.

In one embodiment, the invention provides a MPH extended release powder blend formulation which is reconstitutable into an orally administrable aqueous extended release suspension formulation. Suitably, the MPH extended release powder blend formulation contains, at a minimum, an immediate release methylphenidate component and a sustained release barrier coated methylphenidate-ion exchange resin complex-matrix, optionally further in combination with a water soluble buffering agent. Upon reconstitution of the MPH extended release powder blend into an aqueous suspension formulation by combining with water, the formulation is adjusted to a pH in the range from about 3.5 to about 5, or about 4 to about 4.5, or about 4.2.

In one embodiment, the invention provides an MPH extended release powder blend which contains, at a minimum, both a barrier coated MPH-ion exchanged resin complex-matrix and an uncoated MPH-ion exchange resin complex in combination. This powder blend is designed to be reconstituted for oral delivery as an aqueous suspension. Alternatively, the powder blend can be administered by sprinkling on food (e.g., applesauce), or by other methods. The oral MPH ER powder blend described in the above embodiment contains a dried granular uncoated methylphenidate-ion exchange resin complex and a dried granular barrier coated sustained release methylphenidate-ion exchange resin complex-matrix.

In one embodiment, the powder blend further comprises water-soluble diluent granules which contain at a minimum, a water soluble buffering agent, wherein upon being formulated into an aqueous liquid suspension, the suspension formulation has a pH in the range of about 3.5 to 5, about 4 to about 4.5, or about 4.2. Optionally, excipients including, e.g., one or more of a surfactant, a sweetener, and/or a preservative, may be contained within the diluents granules and thus form a part of the MPH ER powder blend. Alternatively or additionally, these optional excipients may be included in the placebo suspension base. The surfactant may be a poloxamer. The buffering agent may be selected from one or more of an acid selected from the group consisting of citric acid, ascorbic acid, acetic acid, tartaric acid, phosphoric acid, a pharmaceutically acceptable salt of citric acid, ascorbic acid, acetic acid, tartaric acid, phosphoric acid, or a mixture of an acid and a salt. In one embodiment, the buffering agent is a mixture of sodium citrate and anhydrous citric acid.

A "methylphenidate-ion exchange resin complex" refers to the product resulting from loading a methylphenidate salt onto a cation exchange resin. Methods for preparing such complexes have been described, e.g., in WO 2007/109104, incorporated herein by reference. This describes the complexation which occurs when the active and the ion exchange resin are mixed together in an aqueous medium to facilitate the "exchange" between the salt of the MPH and the "cation" of the ion exchange resin and the formation of the complex, which may be referred to as "methylphenidate polistirex".

WO 2007/109104 also describes polyvinylacetate-based barrier coatings which are particularly well suited for use in the formulations described herein to provide a sustained release coat over the MPH-ion exchange resin complex-matrix. However, one skilled in the art can select other barrier coatings to provide the sustained release characteristics to MPH-ion exchange resin complex-matrix.

As used herein, a "precoated" MPH-ion exchange resin complex or a "precoated" MPH-ion exchange resin complex-matrix, refers to a particle which is to be subsequently coated with a barrier coating as defined herein. In some embodiments, where the MPH-ion exchange resin or MPH-ion exchange resin complex-matrix is to be used for the immediate release component and no barrier coating is to be applied, it is referred to as "uncoated".

As used herein, a barrier coat is a water-permeable, water-insoluble, non-ionic polymer or co-polymer which confers modified release and particularly, in the present invention, sustained release for the MPH. As described herein, the barrier coat is applied, e.g., as an aqueous suspension, over the precoated MPH-ion exchange resin complex-matrix and forms a separate layer thereon. Preferably, the barrier coat is directly over the precoated MPH-ion exchange resin complex-matrix and the barrier coat layer, i.e., there are no intervening layers between the barrier coat and the precoated MPH-ion exchange resin complex-matrix. Depending upon the polymeric material selected, the barrier coat polymer or co-polymer may be cured. These polymers and their curing requirements are discussed in more detail elsewhere in this specification.

A "methylphenidate-ion exchange resin complex-matrix" refers a MPH-ion exchange resin complex which is further combined, e.g., prior to or during granulation, with a polymeric material which forms a matrix with the MPH-ion exchange resin complex.

In one embodiment, a "methylphenidate polistirex" refers to the complex (salt) formed by loading methylphenidate onto an ion exchange resin.

The term "matrix forming polymer" or "matrix forming polymeric material" refers to both water-insoluble polymers/co-polymers and water-soluble polymers/co-polymers which form a matrix with the MPH-ion exchange resin complex upon being admixed or granulated therewith. Suitably, the matrix forming polymer is non-reactive with the MPH. The matrix forming polymer may be a water-insoluble polymers/co-polymers and polymer systems which also function as release retardants as described herein, and those hydrophilic polymer systems which have been described in the literature as impregnating or solvating agents. In one embodiment, a MPH-ion exchange resin complex-matrix may include more than one matrix-forming polymer system. For example, an MPH-ion exchange resin complex-matrix may contain both a hydrophilic polymer and a hydrophobic polymer.

The words "comprise", "comprises", and "comprising" are to be interpreted inclusively rather than exclusively. The works "consist", "consisting", and its variants, are to be interpreted exclusively, rather than inclusively.

As used herein the term "about" means a variability of 10% from the reference given, unless otherwise specified.

Methylphenidate/Dexmethylphenidate-Ion Exchange Resin Complex

The active drug component of the extended release powder blend formulation and the extended release aqueous suspension formulation has been described herein as racemic methylphenidate or dexmethylphenidate. These active drugs may be purchased commercially, e.g., methylphenidate HCl and dexmethylphenidate HCl may be purchased. Alternatively, these active compounds may be prepared using methods known to those of skill in the art. Processes for the synthesis of methylphenidate and its analogs have been described. See, e.g., WO 2010/080787; U.S. Pat. Nos. 2,507,631 and 2,957,880, as have processes for synthesis of threo-methylphenidate and its d-enantiomer have been reported. See, e.g., U.S. Patent Application Publication No. 2006/0135777.

A selected MPH can be complexed with, or loaded onto, a cation exchange resin, using methods which are known in the art. See, e.g., WO 2007/109104, and the documents cited therein. Cationic exchange resins are readily selected for use as described herein.

Cationic exchange resins vary in strength, i.e., in their ability to exchange cations. In one embodiment, a relatively strong cationic resin, e.g., Amberlite® IRP69, manufactured by Rohm and Haas (a sulfonated copolymer of styrene and divinylbenzene) is selected. Alternatively, one may select a relatively weak cationic exchange resin, e.g., Amberlite® IRP88 [Rohm and Haas, a crosslinked polymer of methacrylic acid and divinylbenzene)], a weakly acidic (potassium ion) cation exchange resin with 4% cross-linked methacrylate (100 to 500 mesh, equiv to about 150 microns to about 27 microns, ASTM standard) or Amberlite® 64 (a methacrylic acid and divinylbenzene polymer (hydrogen ion) polyacrilex resin, Rohm and Haas, with a particle size ranging from 100 to 400 mesh (equiv to 35 microns to 150 microns, ASTM standard size), capacity ~10 meq/g by dry weight). Further, either regularly or irregularly shaped particles may be used as cation exchange resins according to the present invention. Regularly shaped particles are those particles that substantially conform to geometric shapes such as spherical, elliptical, cylindrical and the like, which are exemplified by Dowex® 50WX8 (The Dow Chemical Company). Irregularly shaped particles are all particles not considered to be regularly shaped, such as particles with amorphous shapes and particles with increased surface areas due to surface channels or distortions. Irregularly shaped ion-exchange resins of this type are exemplified by Amberlite® IRP-69 (manufactured by Rohm & Haas), the use of which is illustrated in the examples below. This cation exchange resin is a sulfonated polymer composed of polystyrene cross-linked with about 8% of divinylbenzene, with an ion-exchange capacity of about 4.5 to 5.5 meq/g of dry resin ($H^+$-form). Another cation exchange resin having similar properties is Dowex® 50WX8 (H+ form, linear formula, $C_{10}H_{12}C_{10}H_{10} \cdot C_8H_8)_x$, 200-400 mesh particle size, which is equivalent to about 75 microns to about 35 microns, ASTM standard). Amberlite® IRP-69 consists of irregularly shaped particles with a size range of about 100 to about 500 mesh (about 150 microns to about 27 microns, ASTM standard). Dowex® 50WX8 is more regularly shaped. Resins are generally purchased with a size ranging from about 25 microns to about 400 microns. However, other sizes may be selected, or larger sized particles may be milled to provide smaller particle sizes.

The selected ion exchange resins may be further treated by the manufacturer or the purchaser to maximize the safety for pharmaceutical use or for improved performance of the compositions. Impurities present in the resins may be removed or neutralized by the use of common chelating agents, antioxidants, preservatives such as disodium edetate, sodium bisulfite, and so on by incorporating them at any stage of preparation either before complexation or during complexation or thereafter. These impurities along with their chelating agent to which they have bound may be removed before further treatment of the ion exchange resin.

The amount of methylphenidate that can be complexed with a resin will typically range from about 5% to about 50% by weight of the MPH-ion exchange resin complex particles. A skilled artisan with limited experimentation can determine the optimum loading for any MPH-ion exchange resin complex. In one embodiment, loading of about 10% to about 40% by weight, more desirably, about 15% to about 30% by weight, or about 25% of the MPH-ion exchange resin complex particles can be employed. In one embodiment, a composition of the invention contains MPH complexed to a sodium polystyrene sulfonate resin in at a ratio of 20 wt MPH (based on the weight of the MPH salt) to 300 wt resin to 80 wt MPH (based on the weight of the salt) to 100 wt resin. In another embodiment, the MPH (based on the weight of the salt) to resin ratio is 4:10 to 1:10, or about 4:10 to about 2:10. In a further embodiment, the dexMPH permits the use of about half the amount of active required when racemic MPH is the active drug.

In one embodiment, following complexation, a MPH-ion exchange resin complex may be, in no particular order, milled to achieve a desired size range and dried (e.g., to a moisture content below about 10%, e.g., about 3% to about 7%), and then stored for future use. In one embodiment, the complex is milled or passed through a sieve to provide a particle size ranging from about 40 microns to about 410 microns to enhance mouth feel (i.e., texture), or about 50 microns to about 250 microns. These particles may be either regularly or irregularly shaped. In some embodiments, the average particle size of the uncoated MPH-ion exchange resin complex or the average particle size of the coated MPH ion exchange resin complex is milled to a size of about 100 to about 200 microns. These particle sizes maybe determined using sieve analysis through a sieve shaker having USP standard wire mesh sieves conforming to ASTM specifications.

In one embodiment, a matrix forming polymer is combined with the MPH-ion exchange resin complex following only partial complexation, or by reducing the moisture content of the wet MPH-ion exchange resin complex to a range of between about 15 to about 25%, or another suitable amount. Treatment of the MPH-ion exchange resin complex with the matrix forming polymer is as follows.

MPH-Ion Exchange Resin Complex-Matrix

Optionally, a matrix-forming polymer is used to assist in processing an uncoated or precoated MPH-ion exchange resin complex. For example, a matrix-forming polymer may be used to facilitate granulation of the immediate release MPH component (e.g., an uncoated MPH-ion exchange resin complex). Alternatively, the matrix-forming polymer may be used for another purpose.

In one embodiment, a polyvinylpyrrolidone polymer [e.g., such as may be purchased commercially as Kollidon® 30] is combined with the methylphenidate-ion exchange resin complex in order to facilitate granulation prior to coating. Other hydrophilic polymeric granulating agents may include water-soluble polymeric materials which have been described in the art as impregnating agents or solvating agents and which function in the present application as granulating agents. In one embodiment, the granulating agent is a polyethylene glycol. Examples of desirable impregnating/solvating agents include those described in U.S. patent application Ser. No. 11/724,966, filed Mar. 15, 2007, Published as US 2007-0215511A, Sep. 20, 2007, and Meadows, US 2003-0099711, which are incorporated herein by reference, or in U.S. Pat. No. 4,221,778 and published US Patent application Publication No. US 2003/009971 A1, the disclosures of which are incorporated herein by reference. Specific examples of other impregnating agents include propylene glycol, polyethylene glycol, polyvinyl alcohol, hydroxypropyl methylcellulose, hydroxypropyl cellulose, and sorbitol.

Optionally, the MPH release rate from the compositions of the present invention may be further prolonged or modified by treating the MPH-ion exchange resin complex prior to the application of the water-permeable diffusion barrier coating described herein, with a release retardant which is a water-insoluble polymer or a combination of a water-insoluble polymers.

The release retardant does not form a separate layer on the MPH-ion exchange resin complex, but forms a matrix therewith. Examples of suitable release retardants include, for example, a polyvinyl acetate polymer or a mixture of polymers containing same (e.g., KOLLICOAT® SR 30D), cellulose acetates, ethylcellulose polymers (e.g., AQUACOAT™ ECD-30 or SURELEASE™), acrylic based polymers or copolymers (e.g., represented by the EUDRAGIT family of acrylic resins), cellulose phthalate, or any combination of such water-insoluble polymers or polymer systems, all herein defined as "release retardants". These retardants when used may further prolong or alter the release of the MPH from the ion exchange resin complex/matrix and maximize attaining the desired release profile. Further, use of release retardant permits in some cases lowering the amount of coating thickness needed to attain a prolonged MPH release of up to about 12 hours. These retardants can be used in either substantially pure form or as a commercial preparation obtained from a vendor. The preferred release retardant is a polyvinyl acetate polymer as described herein or an acrylic polymer from the EUDRAGIT family. Examples of suitable acrylic polymers from the EUDRAGIT family may include, e.g., a copolymer comprising ethyl acrylate and methyl methacrylate (e.g., EUDRAGIT NE-30D), or EUDRAGIT RS, RL30D, RL100, or NE, which are largely pH-independent polymers; although less desirable, certain pH-dependent members polymers including, e.g., members of the EUDRAGIT polymer family, e.g., the L, S, and E, polymers may be selected.

The quantity of polymer that is added to an uncoated or precoated MPH-ion exchange resin complex as a matrix forming polymer typically ranges from about 1% to about 30%, or about 3 to about 20%, or about 3 to about 10%, about 10% to about 15%, about 15 to 25%, or about 1 to about 5% or more by weight of the uncoated or precoated MPH-ion exchange resin particulates prior to their being coated. However, higher or lower amounts may be selected. In one embodiment, where it is desired for the matrix forming polymer to have little or no affect on release rate, a hydrophilic polymer may be selected and used in a higher amount, whereas a hydrophobic release retardant if selected for use will be used at a lower amount. Following admixing, the uncoated or precoated MPH-ion exchange resin complex particles with the matrix forming polymer, the mixture is dried and the MPH-ion exchange resin complex-matrix granules are milled appropriately to the desired particulate size.

For the precoated MPH-ion exchange resin complex-matrix which will be coated and the uncoated MPH-ion exchange resin complex, the particles are milled though a size below about 410 microns, or generally in the range of about 50 microns to about 410 microns, or about 100 microns to about 410 microns. This can be achieved, e.g., using a CO-MIL device fitted with a 40 mesh screen. In one embodiment, the particles have an average size of about 100 to about 250 microns, or about 100 to about 200 microns. In some cases, the milling may be carried out before the complete drying of the complex or complex matrix and then again further drying followed by milling to obtain the desired complex characteristics. These particle sizes maybe determined using sieve analysis through a sieve shaker having USP standard wire mesh sieves conforming to ASTM specifications.

Barrier Coat for Sustained Release

The sustained release component of a MPH extended release powder blend of the invention contains a methylphenidate-ion exchange resin complex-matrix with a barrier coating which modifies the release profile of the methylphenidate-ion exchange resin complex-matrix such that the methylphenidate has about a 12 hour sustained release profile. In one embodiment, the barrier coating layer is about 10% to about 70%, by weight, or about 15% to about 65%, by weight, of the precoated methylphenidate-ion exchange resin complex-matrix in order to provide the sustained release component. In another embodiment, the barrier coating layer is about 20% to about 50%, about 25% to about 40% by weight, about 25% to about 35% by weight, or about 30%, by weight of the precoated methylphenidate-ion exchange resin complex-matrix (i.e., prior to coating).

In one embodiment, the barrier coating is applied as an aqueous dispersion which is dried and cured in order to provide the desired sustained release profile (e.g., polyvinylacetate or ethylcellulose-based coatings). Such a cured barrier coating layer may be in the range of about 15% by weight to about 70% by weight, or about 20% by weight to about 60% by weight, or about 30% by weight to about 45% by weight, based on the total weight of the precoated methylphenidate-ion exchange resin complex-matrix. In another embodiment, the barrier coating is a solvent-based coating system or other polymeric system which does not require curing in order to provide the desired sustained release profile. Such a barrier coating layer (e.g., a Eudragit or Eudragit blend as described herein) may be in the range of about 10% by weight to about 50% by weight, or about 15% by weight to about 45% by weight, or about 25% by weight to about 35% by weight of the precoated methylphenidate-ion exchange resin complex-matrix. Still other suitable ranges can be determined by one of skill in the art, having been provided with the information herein.

In one embodiment, the barrier coating is applied over the MPH-ion exchange complex-matrix as an aqueous dispersion, dried, and milled or passed through a screen such that the barrier coated MPH-ion exchange complex-matrix particles are in the same size range as described in the preceding paragraph, i.e., in the range of about 50 to about 410 microns.

In one embodiment, the aqueous dispersion is a water insoluble polymer comprising a polyvinyl acetate polymer, or a blend of polymers comprising a polyvinyl acetate polymer. In one embodiment, the barrier coating further contains a plasticizer, which can facilitate uniform coating of the MPH-ion exchange resin complex and enhances the tensile strength of the barrier coating layer.

One coating composition useful in the present invention is applied in the form of an aqueous dispersion containing polyvinyl acetate (PVA) polymer based aqueous coating dispersion and a plasticizer. The PVA is insoluble in water at room temperature. The PVA may be used in either substantially pure form or as a blend. Where the barrier coating comprises a PVA polymer, the PVA polymer is present in an amount of about 70% to about 90% w/w of the final barrier coating layer, at least about 75%, at least about 80%, about 85% w/w of the final barrier coating layer. Generally, a plasticizer is used in the percent range, or a mixture of plasticizers combine to total about 2 to about 50% by weight of the coating layer, more preferably about 2.5% to about 20% by weight of the coating layer on the coated MPH-ion exchange resin complex. Preferably a plasticizer is in a range of about 2.5 to about 15% by weight of the coating layer based on the coated complex provides the most desirable properties. Suitable plasticizers may be water soluble and water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin, and Soluphor® P (2-pyrrolidone), and mixtures thereof. Other plasticizers are described in patent application publication US 2003/0099711 A1, May 29, 2003, page 4 (0041) the disclosure of which is incorporated herein by reference.

A commercial polyvinylacetate blend contains primarily a polyvinyl acetate polymer, a stabilizer, and minor amounts of a surfactant such as sodium lauryl sulfate. Where the barrier coating comprises PVP as the stabilizer component, the final barrier coating layer generally contains about 5 to about 10% w/w of polyvinyl pyrrolidone. In one desired embodiment, the aqueous based barrier coating solution is KOLLICOAT® SR 30 D (BASF Corporation) and whose composition is about 27% PVA polymer, about 2.7% polyvinylpyrrolidone (PVP), about 0.3% sodium lauryl sulfate (solids content 30% w/w), mixed with a plasticizer. See, also, U.S. Pat. No. 6,066,334 and U.S. Pat. No. 6,026,277, which is incorporated by reference herein. The PVP and surfactant help stabilize the aqueous dispersion of the PVA. Generally, such stabilizing components are present in an amount totaling less than about 10% w/w, and preferably less than about 5% w/w. Optionally, a selected surfactant is present in an amount of about 1% or less. In one embodiment, the surfactant is a non-ionic surfactant. Optionally, an ionic surfactant may be selected.

In a particularly desirable embodiment, the desired modified release is obtained when the coating layer formed by application of the aqueous dispersion containing the KOLLI-COAT® SR-30D—plasticizer is dried and cured. Preferably, the coating is cured for about 1 to about 24 hours. In alternate embodiments, the coating is cured for about 4 to about 16 hours, and preferably about 5 hours at high temperature, e.g., about 50° C. to about 65° C., and preferably about 60° C. Thus, in one embodiment, the methylphenidate-cation exchange resin complex, matrix has a cured water-permeable, high tensile strength, water insoluble, barrier coating comprising a non-ionic polymer and a plasticizer and having an elongation factor in the range of about 150% to 400%. In one embodiment, the barrier coating comprises a polyvinyl acetate polymer, a stabilizer, a surfactant and a plasticizer. In one embodiment, a barrier coating comprises about 2.5 to about 15% of plasticizer, about 70 to about 90% polyvinylacetate, about 5 to about 10% polyvinylpyrrolidone, and about 0.1 to about 1% surfactant.

Optionally, another barrier coating may be selected. See, e.g., the barrier coatings described in Kolter et al, U.S. Pat. No. 6,066,334 and U.S. Pat. No. 6,046,277 and Mehta et al, US Published Patent Application No. US 2007-0215511A, published Sep. 20, 2007, and its counterpart application, WO 2007/109104, which are incorporated herein by reference. See, also, e.g., Wen, U.S. Pat. Nos. 6,046,277 and 6,001,392; Meadows, US Published Patent Application No. 2003/009971 and related application WO 03/020242; Sovereign Pharmaceuticals, WO 2006/022996 and related applications US Published Patent Application Nos. US2005/232986; US2005/232987; US2005/232993; US2005/266032.

Alternatively, other known aqueous or non-aqueous barrier coatings have been described in the literature and/or which are commercially available could be used for the coating process, but are less desirable for the reasons described in US Patent Publication No. US 2007-0215511A and in the literature cited in the background therein. See, e.g., Bess, et al, U.S. Pat. No. 7,067,116; Goede et al, U.S. Pat. No. 6,667,058, Wen et al, U.S. Pat. No. 6,001,392, among others. Such coating materials include ethylcellulose based extended release coatings, e.g., Aquacoat™ ethylcellulose polymer extended release coating and Surelease®. Surelease® is available from Colorcon as an aqueous ethyl cellulose dispersion containing water (70.6% w/w), ethylcellulose (18.8% w/w), ammonium hydroxide (4.4% w/w), a medium chain triglyceride (4.0% w/w), and oleic acid (2.2% w/w).

In one embodiment, the coating may be a EUDRAGIT™ brand acrylate based coating materials [including, e.g., a poly (ethyl acrylate-co-methyl methacrylate-co-trimethylammonioethyl methacrylate chloride) polymer system]. For example, Eudragit™ RS 30D [a pH-independent, 30% aqueous dispersion of poly(ethyl acrylate-co-methyl methacrylate-co-trimethylammonioethyl methacrylate chloride) 1:2:0.1)], or Eudragit™ RL 30D [a 30% aqueous dispersion, pH independent polymer, poly(ethyl acrylate-co-methyl methacrylate-co-trimethylammonioethyl methacrylate chloride) 1:2:0.2)] may be selected as the barrier coating. In one embodiment, a blend of Eudragit™ RS 30D and Eudragit™ RL 30D may be prepared to optimize the hydrophilicity/hydrophobicity of the film in order to achieve desirable release profiles. Optionally, talc may be mixed with one of the Eudragit™ products to improve flow during coating and to address issues of tackiness of the product during processing. Typically, the coating layer resulting from application of this blend is not subject to any curing.

MPH-Extended Release Powder Blend

In order to achieve the desired profile, an oral methylphenidate powder according to the invention is a blend of an immediate release methylphenidate component and a sustained release methylphenidate component. In one embodiment, the blend contains about 5 to about 30%, or about 10% to about 25%, or about 20% immediate release MPH component to about 70 to about 95%, about 75% to about 90%, by weight, or about 80% by weight sustained release MPH component, based on the total weight of the MPH. However, these ratios can be adjusted as desired.

In one embodiment, the immediate release component is an uncoated methylphenidate-resin complex and the sustained release component is a barrier coated methylphenidate-ion exchange resin complex-matrix. In another embodiment, an immediate release component can be a methylphenidate-ion exchange resin complex having a coating layer as described herein such that the layer is either thin enough or uncured so that it provides immediate release. This layer does not interfere with the immediate release of the drug. For example, such an immediate release coated methylphenidate-ion exchange resin complex may contain less than about 10% by weight a coating layer, or about 1% to about 8%, by weight, or less. In other embodiments, the immediate release methylphenidate-ion exchange resin complex may contain a higher weight percentage of an aqueous-based coating system such as the polyvinyl acetate or ethylcellulose system, if the coating layer is not cured. Optionally, the immediate release component may be in a matrix with a polymer which does not significantly alter its release profile, i.e., the immediate release methylphenidate-ion exchange resin complex-matrix is an immediate release as defined above. In other words, an "immediate release" MPH component preferably releases in less than 1 hour, e.g., as soon as about 45 minutes or as soon as about 30 minutes. Further, in one embodiment, the MPH immediate release component releases at least about 50% of the MPH within about the first hour following administration, and at least about 80% of the MPH within about 90 minutes following administration.

In one embodiment, the powder blend also contains a diluent granule, which facilitates reconstitution of the particulate MPH-ion exchange resin complex, particulate coated MPH-ion exchange resin complex-matrixes and optionally also provides agents for improving the flow of the powder (e.g., glidants), sweeteners or other flavorings, or suspending agents.

In one embodiment, a diluent granule used in the invention contains a buffering species used to control pH in the liquid suspension formulation. Optionally, the diluents granule may contain one or more other excipients including, e.g., a glidant, a flavoring agent, a preservative, a suspending agent, or mixtures of such excipients.

Suitably, the buffering species is selected so that upon being combined with water and any other components of a placebo suspension base, the final oral aqueous liquid suspension formulation has a pH in the range of about 3.5 to 5, about 4 to about 4.5, or about 4.2. The surfactant may be a poloxamer. The buffering agent may be selected from one or more of an acid selected from the group consisting of citric acid, ascorbic acid, acetic acid, tartaric acid, phosphoric acid, a pharmaceutically acceptable salt of citric acid, ascorbic acid, acetic acid, tartaric acid, phosphoric acid, or a mixture of an acid or salt. In one embodiment, the buffering agent is a mixture of sodium citrate and anhydrous citric acid. As described herein, the diluent granules further comprise one or more of a poloxamer, a sweetener, and a preservative.

One suitable non-ionic polyoxyethylene-polyoxypropylene block co-polymers (poloxamers), is represented by the formula: $HO(C_2H_4O)_a(C_3H_6O)_b(C_2H_4O)_aH$. The examples below illustrate the use of Poloxamer 188 (available as Pluronic F68 from BASF), where in the formula above "a" is 86 and "b" is 27. However, other suitable poloxamers, or other diluents may be selected. The surfactants useful in the preparation of the finished compositions of the present invention are generally organic materials which aid in the stabilization and dispersion of the ingredients in aqueous systems for a suitable homogenous composition. Preferably, the surfactants of choice are non-ionic surfactants such as poly(oxyethylene) (20) sorbitan monooleate and sorbitan monooleate. These are commercially known as TWEENS and SPANS and are produced in a wide variety of structures and molecular weights.

Whereas any one of a number of surfactants may be used, preferably a compound from the group comprising polysorbate copolymers (sorbitan-mono-9-octadecenoate-poly(oxy-1,2-ethanediyl)) is employed. This compound is also added functions to keep any flavors and sweeteners homogeneously dissolved and dispersed in solution.

Suitable polysorbates include polysorbate 20, polysorbate 40, polysorbate 80 and mixtures thereof. Most preferably, polysorbate 80 is employed. The surfactant component will comprise from about 0.01 to about 2.0% w/v of the total composition and preferably will comprise about 0.1% w/v of the total weight of the composition.

A second emulsifier/surfactant useful in combination with polysorbates may be employed and is preferably a poloxamer such as Poloxamer 407. Poloxamer 407 has an HLB (hydrophilic/lipophilic balance) of about 22 and is sold under the tradename Pluronic-127 (BASF-NJ). The two surfactants can be employed in substantially equivalent amounts. For example, the Poloxamer 407 and polysorbate 80 may each be employed together at levels of approximately from about 0.02 to about 4.0% w/v of the total weight of the formulation.

In the instance where auxiliary sweeteners are utilized, the present invention contemplates the inclusion of those sweeteners well known in the art, including both natural and artificial sweeteners. Thus, additional sweeteners may be chosen from the following non-limiting list: Water-soluble sweetening agents such as monosaccharides, disaccharides and polysaccharides such as xylose, ribose, glucose, mannose, galactose, fructose, high fructose corn syrup, dextrose, sucrose, sugar, maltose, partially hydrolyzed starch, or corn syrup solids and sugar alcohols such as sorbitol, xylitol, mannitol and mixtures thereof.

In general, the amount of sweetener will vary with the desired amount of sweeteners selected for a particular liquid formulation. This amount will normally be 0.001 to about 90% by weight, per volume of the final liquid composition, when using an easily extractable sweetener. The water-soluble sweeteners described above, are preferably used in amounts of about 5 to about 70% by weight per volume, and most preferably from about 10 to about 50% by weight per volume of the final liquid composition. In contrast, the artificial sweeteners [e.g., sucralose, acesulfame K, and dipeptide based sweeteners] are used in amounts of about 0.005 to about 5.0% and most preferably about 0.01 to about 2.5% by weight per volume of the final liquid composition. These amounts are ordinarily necessary to achieve a desired level of sweetness independent from the flavor level achieved from flavor oils.

Suitable flavorings include both natural and artificial flavors, and mints such as peppermint, menthol, artificial vanilla, cinnamon, various fruit flavors, both individual and mixed, essential oils (i.e. thymol, eucalyptol, menthol and methyl salicylate) and the like are contemplated. The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. The flavorings are generally utilized in amounts that will vary depending upon the individual flavor, and may, for example, range in amounts of about 0.01 to about 3% by weight per volume of the final composition weight.

Useful preservatives include, but are not limited to, sodium benzoate, benzoic acid, potassium sorbate, salts of edetate (also known as salts of ethylenediaminetetraacetic acid, or EDTA, such as disodium EDTA), parabens (e.g., methyl, ethyl, propyl or butyl-hydroxybenzoates, etc.), and sorbic acid. Amongst useful preservatives include chelating agents some of which are listed above and other chelating agents, e.g., nitrilotriacetic acid (NTA); ethylenediaminetetracetic acid (EDTA), hydroxyethylethylenediaminetriacetic acid (HEDTA), diethylenetriaminepentaacetic acid (DPTA), 1,2-Diaminopropanetetraacetic acid (1,2-PDTA); 1,3-Diaminopropanetetraacetic acid (1,3-PDTA); 2,2-ethylenedioxybis[ethyliminodi(acetic acid)] (EGTA); 1,10-bis(2-pyridylmethyl)-1,4,7,10-tetraazadecane (BPTETA); ethylenediamine (EDAMINE); Trans-1,2-diaminocyclohexane-N,N,N',N'-tetraacetic acid (CDTA); ethylenediamine-N,N'-diacetate (EDDA); phenazine methosulphate (PMS); 2,6-Dichloro-indophenol (DCPIP); Bis(carboxymethyl)diaza-18-crown-6 (CROWN); porphine; chlorophyll; dimercaprol (2,3-Dimercapto-1-propanol); citric acid; tartaric acid; fumaric acid; malic acid; and salts thereof. The preservatives listed above are exemplary, but each preservative must be evaluated in each formulation, to assure the compatibility and efficacy of the preservative. Methods for evaluating the efficacy of preservatives in pharmaceutical formulations are known to those skilled in the art. Preferred preservatives are the paraben preservatives include methyl, ethyl, propyl, and butyl paraben. Methyl and propyl paraben are most preferable. Preferably, both methyl and propyl paraben are present in the formulation in a ratio of methyl paraben to propyl paraben of from about 2.5:1 to about 16:1, preferably 9:1.

Optionally, these diluents granules as described herein may form part of the MPH extended release powder blend formulation. When present, the diluents granules may be in amount of about 1% by weight to about 90%, or about 10% to about 85%, or about 50% to about 75% by weight of the total MPH extended release powder blend.

In one embodiment, the invention provides a methylphenidate ER powder blend containing a barrier coated MPH-ion exchange resin complex-matrix which provides a sustained release MPH profile following administration, an uncoated MPH-ion exchange resin complex, or another immediate release MPH component, and an optional pH adjuster which is a compound selected to adjust the pH of a suspension formed by combining water and the methylphenidate ER powder blend to about 3.5 to about 5, about 4 to about 5, about 4 to about 4.5, or about 4.2. Suitable pH adjusters, including various excipients, may be selected. A pH adjuster may be a buffering agent as described herein.

The ratio of immediate release MPH component to sustained release MPH component may be adjusted as desired by one of skill in the formulation art. In one embodiment, the powder blend contains about 5 to about 20 parts by weight MPH in immediate release form and about 95 to about 80 parts by weight MPH in the sustained release barrier coated MPH-ion exchange resin complex-matrix, based the total weight of MPH in the blend (i.e., excluding the other components such as the ion exchange resin, matrix forming polymer and coating). In another embodiment, the MPH ER powder blend contains about 10 to about 30 parts by weight MPH in immediate release form to about 90 to about 70 parts by weight MPH in sustained release barrier coated MPH-ion exchange resin complex-matrix, based upon the total weight MPH. In still a further embodiment, the MPH ER powder blend contains about 20 parts by weight MPH in immediate release form to about 80 parts by weight sustained release MPH, based upon the total weight methylphenidate in the powder blend. In one particularly preferred embodiment, the immediate release MPH is in a complex with an ion exchange resin as described herein, optionally further in combination with a matrix forming agent. As described herein, the MPH-ion exchange resin complex and the barrier coated MPH-ion exchange resin complex-matrix are in particulate form and have been processes to ensure that they have a size of about 50 to about 410 microns, preferably below about 410 microns. Typically, the average size of the particulates is in the range of about 100 microns to about 250 microns in size.

In one embodiment, the MPH extended release powder blend is formulated in a dosage unit which comprises a mixture of granular, barrier coated MPH-ion exchange resin complex-matrix and uncoated MPH-ion exchange resin complexes, said granular matrix and complex having a particle size ranging from about 40 microns to about 410 microns to enhance mouth feel (i.e., texture), or about 50 microns to about 250 microns. These particles may be either regularly or irregularly shaped. In some embodiments, the average particle size of the uncoated MPH-ion exchange resin complex-matrix or the average particle size of the coated MPH-ion exchange resin complex-matrix is milled to a size of about 100 to about 200 microns. These particle sizes may be determined using sieve analysis through a sieve shaker having USP standard wire mesh sieves conforming to ASTM specifications. Because the diluent granule is water-soluble, the average size of these granules may be larger than those of the uncoated MPH-ion exchange resin complex and the barrier coated MPH-ion exchange resin complex-matrix. In fact, a larger granule size may be desirable as the larger surface area of such granules facilitates dissolution of the diluent granule upon being combined with water. In one embodiment, the diluent granules are milled through a Fitz mill or other similar device fitted with a 20 mesh screen. Thus, in one embodiment, the diluent granules are a size below about 850 microns (μm), or below about 840 μm. However, diluent granules may be milled to a smaller size, e.g., about 100 μm to about 200 μm, or to a larger size, e.g., up to about 1000 μm. In one embodiment, the MPH extended release powder blend is a homogenous mixture of the granular, barrier coated MPH-ion exchange resin complex-matrix particles and the granular, uncoated MPH-ion exchange resin complex particles having a size ranging from about 100 μm to about 410 μm, in a homogenous admixture with diluent granules, which may range in size from about 100 μm to about 1000 μm.

The MPH extended release powder is stable over a period of at least about 18 months at room temperature and has been tested for least 6 months under accelerated conditions which are predictive of stable shelf-life for at least about 24 months. As is illustrated in the examples herein, the potency of the MPH (the active component of the compositions of the invention) is not directly related to the primary degradation product. In some embodiments, the MPH extended release powder blend has less than 5% loss in potency, preferably less than 3% loss of potency, over a period of at least about 18 months under ambient conditions. While useful for formulation as a solid, the MPH extended release powder blend can be prepared as a suspension for oral delivery at the time the product needs to be used. This MPH suspension has a stable shelf-life under ambient conditions over a period of at least about four months at room temperature following admixing with water to form the aqueous extended release MPH suspension. In some embodiment, an aqueous MPH suspension containing the MPH ER powder blend has less than 5% loss in potency, preferably a less than 3% loss of potency, over a period of at least about 4 months at room temperature.

In one embodiment, the MPH extended release powder blend is formed into a solid unit dose or a solid preparation. Such solid preparations may take the form of the powder, optionally with further excipients, loaded into a foil packet, sachet or the like, or other solid preparations such as tablets or capsules, etc. In one embodiment, a tablet of the invention is formulated as an orally disintegrating tablet. Such orally dissolving tablets may disintegrate in the mouth in less than about 60 seconds.

In another embodiment, the MPH extended release powder which can be readily prepared as a suspension for oral delivery. Once prepared as an oral aqueous suspension, the resulting suspension provides a product which can be stored for at least about one month, or at least about four months, as a suspension.

Orally Administrable Aqueous MPH Extended Release Suspensions

In one aspect, the invention provides a methylphenidate aqueous extended release oral suspension comprising at least 50% by weight water based on the total weight of the liquid component of the suspension, wherein extended release is as defined herein (e.g., provides a therapeutically effective plasma profile for about 12 hours). In one embodiment, the suspension contains at least about 80% by weight based on the total weight of the suspension. In one embodiment, the suspension has a pH of about 3.5 to about 5. In another embodiment, the suspension has a pH of about 4 to about 5, or about 4 to about 4.5, or about 4.2.

In one embodiment, where the methylphenidate aqueous extended release oral suspension contains at least one coated methylphenidate-ion exchange resin complex-matrix comprising methylphenidate bound to a pharmaceutically acceptable ion exchange resin and having a high tensile strength water-permeable, water-insoluble, non-ionic polymeric barrier coating, the suspension contains at least one other source of a drug (e.g., methylphenidate or a different drug). In one embodiment, the high tensile strength water-permeable, water-insoluble, non-ionic polymeric barrier coating is a cured, coated (Kollicoat® SR30D—plasticizer) barrier coating.

In one embodiment, wherein the methylphenidate aqueous extended release oral suspension contains as the sustained release or modified release component at least one coated methylphenidate-ion exchange resin complex comprising methylphenidate bound to a pharmaceutically acceptable ion exchange resin and having a high tensile strength water-permeable, water-insoluble, non-ionic polymeric barrier coating, the suspension also contains an immediate release methylphenidate component.

In one embodiment, a methylphenidate aqueous extended release oral suspension has a pharmacokinetic profile in which d-methylphenidate has an $AUC_{0-\infty}$ of about 114 ng-hr/mL to about 180 ng-hr/mL, $C_{max}$ of about 11 ng/mL to about 17 ng/mL, $T_{max}$ of about 4 hours to about 5.25 hours and $T_{1/2}$ of about 5 hours to about 7 hours following a single oral administration of an aqueous liquid suspension at a dose equivalent to 60 mg racemic MPH in adults. In one embodiment, the methylphenidate aqueous extended release oral suspension has a pharmacokinetic profile of FIG. 3 and/or a pharmacokinetic profile in which d-methylphenidate has an $AUC_{0-\infty}$ of about 143.65 ng-hr/mL, $C_{max}$ of about 13.61 ng/mL, $T_{max}$ of about 5 hours and $T_{1/2}$ of about 5.65 hours following a single oral administration of an aqueous liquid suspension at a dose equivalent to 60 mg racemic MPH in adults.

In one embodiment, the methylphenidate aqueous extended release oral suspension has a pharmacokinetic profile in which methylphenidate has an $AUC_{0-\infty}$ of about 137.2 to about 214.4 ng-hr/mL, a $C_{max}$ of about 13.6 to about 21.3 ng/mL, $T_{max}$ of about 3 to about 5 hours, or about 3.5 to about 4 hours, or about 3.77 hours, following a single oral administration of an aqueous liquid suspension at a dose equivalent to 72 mg racemic MPH in adults. For example, the suspension may have the pharmacokinetic profile of FIG. 1 in which d-methylphenidate has an $AUC_{0-\infty}$ of about 171.5 ng-hr/mL and a $C_{max}$ of about 17.0 ng/mL following a single oral administration of an aqueous liquid suspension at a dose equivalent to 72 mg racemic MPH in adults.

In one embodiment, the methylphenidate aqueous extended release oral suspension contains methylphenidate selected from racemic methylphenidate and/or dexmethylphenidate.

In another embodiment, the invention provides an aqueous liquid suspension formulation reconstituted from a powder blend. The powder blend typically contains granules of a size ranging from about 50 to about 410 μm in size, which granules are a blend of uncoated methylphenidate-ion exchange resin complex, a barrier coated methylphenidate-ion exchange resin complex-matrix, and, optionally, a diluent granule. Where a diluent granule is present in the MPH ER powder blend, upon admixing with the aqueous liquid suspension, the diluent granule is dissolved and forms a solution, whereas the uncoated MPH-ion exchange resin complex and the coated MPH-ion exchange resin complex-matrix are suspended. Optionally, a pH adjuster may be provided by the diluent granule or this function may be provided by a separate component when the powder is combined to farm the suspension. Such a pH adjuster is a component which adjusts the pH of the suspension to the range of about 3.5 to about 5, about 4 to about 5, about 4 to about 4.5, or about 4.2.

Optionally, one or more desired excipients, including, e.g., flavorants, sweeteners, or preservatives, or other excipients may be added to the suspension.

In one embodiment, an orally administrable aqueous suspension is obtained by dispersing the MPH extended release powder blend in a suitable aqueous vehicle (i.e., water). When reference is made to an oral aqueous suspension, the term encompasses products containing the MPH ER powder blend suspended in a liquid base which contains more than about 50% water. In some embodiments, the liquids in the aqueous suspension base contain at least about 80% water, at least about 90% water, at least about 95% water, at least about 99% water, or 100% water. Suitably, the suspension has a pH in the range of about 3.5 to about 5, preferably, about 4 to about 4.5 and more preferably about 4.2. In some embodiments, the liquid suspension contains at least 80% water and the resulting formulation is stable for at least about one month following combination of the components of the MPH powder blend and the aqueous suspension. In some embodiments, the MPH aqueous ER suspension is stable for at least about four months.

The MPH extended release aqueous suspension product permits ready dose titration, i.e., adjusting the dose of a medication based on recommended dose range and frequency until the desired therapeutic effect is achieved. With the MPH ER aqueous suspension, physician can titrate as rapidly or slowly as desired, using any dose increment; in contrast, with tablets and other similar solid formulations, the dose increment is limited. In addition, a physician can readily customize the dose so it is precisely right for the patient. This is particularly desirably, as many patients experience some side effects (i.e., difficulty sleeping or loss of appetite) as they approach or slightly exceed the therapeutic dose. Since most doctors prefer extended release dosage forms for these patients (so they don't need to take a $2^{nd}$ dose during the day), customizing dose and good dose titration was difficult using the products available prior to this invention. The present product will provide an extended release aqueous suspension MPH medication, making it useful for titration and once daily dosing.

In one embodiment, the MPH ER powder blend provides a pharmacokinetic profile in which d-methylphenidate has $AUC_{0-\infty}$ (ng-hr/mL) of about 114 ng-hr/mL to about 180 ng-hr/mL, $C_{max}$ (ng/mL) is about 11 (ng/mL) to about 17 (ng/mL), $T_{max}$ (hr) is about 4 hours to about 5.25 hours and $T_{1/2}$ (hr) is about 5 hours to about 7 hours following a single oral administration of an aqueous liquid suspension containing the MPH ER powder blend suspended therein at a dose equivalent to about 60 mg racemic methylphenidate hydrochloride in adults. In one embodiment, the MPH ER powder blend contains racemic methylphenidate. In another embodiment, the MPH ER powder blend contains dexmethylphenidate. In still another embodiment, the MPH ER powder blend contains both racemic methylphenidate and dexmethylphenidate. In one embodiment, an MPH ER powder blend comprising an immediate release methylphenidate component, a sustained release barrier coated methylphenidate-ion exchange resin complex-matrix, and an optional water soluble buffering agent, provide this pharmacokinetic profile. In one embodiment, the blend contains about 5 to about 30%, or about 10% to about 25%, or about 20% immediate release MPH component to about 70 to about 95%, about 75% to about 90%, by weight, or about 80% by weight sustained release MPH component, based on the total weight of the MPH. In one embodiment, the immediate release component is an uncoated MPH-ion exchange resin complex may provide the immediate release component. However, optionally, other immediate release forms of the MPH may be utilized in a formulation of the invention. Where the immediate release methylphenidate component is an uncoated methylphenidate-ion exchange resin complex, it is optionally in combination with a hydrophilic or hydrophobic polymeric matrix forming component as defined herein. The sustained release MPH component is a barrier coated MPH-ion exchange resin complex-matrix. In one embodiment, the barrier coating is a water-permeable, high tensile strength, water insoluble, barrier coating comprising a polyvinylacetate polymer and a plasticizer. In another embodiment, the barrier coating is an ethylcellulose barrier coating. In still another embodiment, the coating is a poly(ethyl acrylate-co-methyl methacrylate-co-trimethylammoniumethylmethacrylatechloride) polymer. Depending upon the barrier coating selected, curing is optional, as described in more detail in this specification, which discussion is incorporated by reference herein. In one embodiment, the barrier coating is cured and comprises a polyvinylacetate, a stabilizer, a surfactant, and a plasticizer. In one embodiment, the barrier coat comprises about 2.5 to about 15% of plasticizer, about 70 to about 90% polyvinylacetate, about 5 to about 10% polyvinylpyrrolidone, and about 0.1 to about 1% surfactant. In a further embodiment, the plasticizer is triacetin and the surfactant is sodium lauryl sulfate. In still a further embodiment, the barrier coat comprises about 20% to about 45% by weight of the coated methylphenidate-ion exchange resin complex-matrix. In another embodiment, the coated methylphenidate ion exchange resin complex-matrix comprises a hydrophilic polymer in an amount of about 5 to about 20% by weight, based on the weight of the uncoated methylphenidate-ion exchange resin complex-matrix. In still a further embodiment, the hydrophilic polymer is polyvinylpyrrolidone. In another embodiment, the coated methylphenidate ion exchange resin complex-matrix comprises a hydrophobic polymer or co-polymer in an amount of about 5 to about 20% by weight, based on the weight of the (uncoated or precoated) methylphenidate-ion exchange resin complex-matrix. In still a further embodiment, the hydrophobic polymer comprises polyvinylacetate. Optionally, in any of the embodiments described herein, the MPH ER powder blend may contain water-soluble diluent granules in order to facilitate suspension and provide a powder blend to which only water need be added to provide a final suspension suitable for administration to a patient. The pH adjuster may be a buffering agent which may include one of the following or may be selected from the group consisting of one or more of a pharmaceutically acceptable acid selected from the group consisting of citric acid, ascorbic acid, acetic acid, tartaric acid, phosphoric acid, a pharmaceutically acceptable salt of citric acid, ascorbic acid, acetic acid, tartaric acid, phosphoric acid, or a mixture of said pharmaceutically acceptable acid or salt. In one embodiment, the buffering agent contains a mixture of sodium citrate and anhydrous citric acid. In another embodiment, the diluent granules further comprise one or more of a surfactant, a sweetener, and a preservative. In a further embodiment, the diluent granules comprise a poloxamer.

In one embodiment, the powder blend is reconstituted into an aqueous liquid MPH extended release suspension formulation having a pharmacokinetic profile in which d-methylphenidate has $AUC_{0-\infty}$ is about 143.65, $C_{max}$ (ng/mL) is about 13.61, $T_{max}$ (hr) is about 5 and $T_{1/2}$ (hr) is about 5.65.

In one embodiment, an MPH ER powder blend having the following formula has this profile a cured, (Kollicoat® SR30D—plasticizer) barrier coated (30% weight gain) methylphenidate-ion exchange resin complex-polyvinylpyrrolidone (about 8%) matrix,) an uncoated methylphenidate-ion exchange resin complex, in which the weight ratio of immediate extended release MPH to sustained release MPH is approximately 80 parts by weight to approximately 20% parts. In one embodiment, the powder blend is reconstituted into an aqueous liquid MPH extended release suspension formulation having a pharmacokinetic profile in which d-methylphenidate has $AUC_{0-\infty}$ is about 143.65, $C_{max}$ (ng/mL) is 13.61 (42.56), $T_{max}$ (hr) is 5.00 (1.67-6.00) and $T_{1/2}$ (hr) is 5.65 (15.01) at a dose equivalent to about 60 mg racemic methylphenidate hydrochloride in adults.

In still another embodiment, the present invention provides a single MPH extended release product which provides immediate release and further provides the pharmacokinetic profile of a twelve-hour sustained release composition. In one embodiment, the extended release contains an immediate release component which is bioequivalent to a commercially available immediate release formulation (e.g., Methylin) and a component providing a sustained release MPH profile.

In one embodiment, the oral MPH aqueous ER suspension has a pH in the range of about 3.5 to about 5, preferably, about 4 to about 4.5 and more preferably about 4.2. In some embodiments, the aqueous suspension contains at least 80% water and the resulting formulation is stable for at least about one month following combination of the MPH ER powder blend and the suspension base. In other embodiments, the Aqueous suspension is stable at a pH of about 4 to about 4.5 for at least about four months following preparation of the suspension containing the MPH ER powder blend.

Uses

An aqueous MPH extended release composition of the invention may be orally administered to a patient having a disorder treatable by MPH. These include disorders for which regulatory approval has been granted in the US or other jurisdiction in which the drug is being administered and which requires regulatory approval. For example, MPH is currently approved for treatment of Attention Deficit Hyperactivity Disorder (ADHD), postural orthostatic tachycardia syndrome, and narcolepsy. MPH has also been described in patent applications and in the literature as being useful for treatment of such disorders including, but are not limited to, behavioral disorders, treatment-resistant cases of lethargy, depression, neural insult, obesity, and rarely other psychiatric disorders such as obsessive-compulsive disorder, Attention Deficit Disorder, depression, specific dyslexias, brain dysfunction, cognitive decline in AIDS and AIDS related conditions, alertness in geriatric, Alzheimer's patients, in recovery in stroke victims.

Thus, the invention provides a method of treating one or more of the above disorders for a period of at least twelve hours by administering an aqueous oral liquid MPH extended release composition based on the reconstituted MPH extended release powder blend of a barrier coated methylphenidate-ion exchange resin complex-matrix and MPH immediate release component (e.g., an uncoated MPH-ion exchange resin complex), e.g., a liquid suspension product having a pH in the range of about 3.5 to about 5, about 4 to about 5, about 4 to about 4.5 or about 4.2. Following administration of a single dose of the oral MPH composition, a therapeutically effective amount of MPH is reached as soon as about 45 minutes or earlier. In one embodiment, the average peak plasma concentration from a single oral dose of the MPH extended release aqueous suspension is reached about two to about five hours after administration.

The concentration of methylphenidate is variable and may be determined by the desired dosage and volume. For example, an amount of methylphenidate equivalent to 1 mg/mL methylphenidate HCl may be used to provide a 5 mg oral dose per teaspoon, and an amount of methylphenidate equivalent to 2 mg/mL methylphenidate HCl suspension may yield a 10 mg oral dose per teaspoon. These concentrations correspond to two dosages currently available, but can go higher. However, since the methylphenidate is delivered in a solution, the dosage can be easily manipulated to prescribe a non-standard dosage. The concentration of methylphenidate may be equivalent to about 0.1 mg/mL to about 10.0 mg/mL methylphenidate HCl.

A composition of the invention is formulated to deliver MPH is, most desirably, in dosages ranging from about 1 mg up to about 100 mg per day, preferably from about 10 to about 75 mg per day, or in about 18, 25, or 60 mg doses [based on equivalence to racemic methylphenidate HCl] although variations will necessarily occur depending upon the weight and condition of the subject being treated and the particular route of administration chosen. Actual dosages of dexmethylphenidate may be at half the amounts of racemic methylphenidate. Variations may nevertheless occur depending upon the weight and condition of the persons being treated and their individual responses to said medicament.

As described herein, the MPH extended release composition of the invention permits the compounds to be dosed orally twice-a-day at 12-hour intervals. However, depending upon the patient, smaller doses may be delivered at intervals during the day. Other patients may take a single dose in the morning and forego dosage in the evening.

The following examples are illustrative only and are not intended to be a limitation on the present invention.

EXAMPLES

Examples 1 to Examples 5 illustrate preparation of powders which are reconstitutable for methylphenidate-ion exchange resin oral suspension, equivalent to 25 mg Methylphenidate HCl per 5 mL.

Example 1

Methylphenidate ER Powder for Aqueous Oral Suspension

Example 1 illustrates preparation of an oral suspension composition reconstituted from a methylphenidate (MPH) extended release (ER) powder. In this example, the MPH ER powder blend is a combination of (i) an uncoated methylphenidate-ion exchange resin, (ii) a cured, coated (polyvinylacetate-plasticizer, 30% weight gain) methylphenidate-ion exchange resin complex-hydrophilic polymer matrix, and (iii) diluent granules.

A. Uncoated Methylphenidate-Ion Exchange Resin Complex

| Ingredients | Quantity |
|---|---|
| Methylphenidate HCl | 3100 g |
| Amberlite ® IRP 69 Sodium Polystyrene Sulfonate Resin | 7693 g |
| Purified Water* | Qs* |

*Removed during processing

The uncoated methylphenidate-resin complex was prepared by first adding 80 L of Purified Water in to the vessel and methylphenidate HCl was dissolved by continuous mixing. Sodium Polystyrene Sulfonate ion exchange resin [Amberlite® IRP 69; Rohm and Haas] was dispersed in the solution with continuous mixing, which was continued for 60 minutes to permit time for the methylphenidate and ion exchange resin to form a complex. Water was removed by filtration process followed by rinsing twice using purified water; during which process displaced salt ions (from the MPH or the resin) are also removed. Wet resin complex was then dried until moisture content was 3% to 7%. This dried methylphenidate-ion exchange resin complex was passed through a CO-MIL device fitted with a standard 40 mesh screen (i.e., the granules passing through have a particulate size below about 410 μm). This was the particulate uncoated Methylphenidate-resin complex (methylphenidate polistirex).

B. Precoated Methylphenidate-Ion Exchange Resin Complex-Matrix

| Ingredients | Quantity |
|---|---|
| Uncoated Methylphenidate - Ion Exchange Resin Complex of Part A | 8500 g |
| Kollidon ® K30 polyvinylpyrrolidone (PVP) | 657 g |
| Purified water* | 2629 g |
| Purified Water* | Qs* |

*Removed during processing

In a separate container polyvinylpyrrolidone (purchased as Kollidon® K30 from BASF) was dissolved in 2629 gms of Purified Water (PVP solution). Uncoated methylphenidate-resin complex prepared according to Part A was treated with the povidone solution until a 7.73% polymer weight gain was achieved and with continuous mixing to form a uniform mass. The wet mass was dried until the moisture content was between 15-25%. Semi-dried material was then passed through a CO-MIL device fitted with a standard 40 mesh screen (about 410 µm). Milled material was further dried until moisture content was 3% to 7%. Dried material was again passed through a CO-MIL device fitted with a standard 40 mesh screen (about 410 µm). This was the precoated methylphenidate-ion exchange resin complex-(PVP) matrix.

C. Coated Methylphenidate-Ion Exchange Resin Complex-Matrix

| Ingredients | Quantity |
|---|---|
| Precoated Methylphenidate - Ion Exchange Resin Complex - Matrix of Part B | 3900 g |
| Kollicoat ® SR30D (30% w/w aqueous dispersion* | 3714 g |
| Triacetin (plasticizer) | 56 g |
| Purified Water* | 2080 g |

*Removed during processing

The precoated methylphenidate-ion Exchange Resin complex-matrix was coated as follows. The coating solution was prepared by mixing Triacetin, Purified Water and Kollicoat® SR30D (BASF, aqueous dispersion with 30% solids content, containing 27% Polyvinylacetate, 2.7% polyvinylpyrrolidone, 0.3% sodium lauryl sulfate) in a separate container. The coating process was performed in a fluid bed processor equipped with Wurster column by applying coating solution on to 3900 grams of the precoated methylphenidate-ion exchange resin complex-matrix prepared as described in Part B above, until 30% weight gain was achieved. The (Kollicoat® SR30D—triacetin) coated methylphenidate-ion exchange resin complex-matrix was cured in a hot air oven at 60° C. for 5 hours. The cured coated methylphenidate-ion exchange resin complex-matrix was passed through a standard 40 mesh screen.

D. Diluent Granules

| Ingredient | Quantity |
|---|---|
| Poloxamer 188 | 125 g |
| Purified water* | 1764 g |
| Sugar | 34418 g |
| Sodium citrate | 965 g |
| Anhydrous citric acid | 1290 g |
| Sodium benzoate | 500 g |
| Sucralose | 200 g |

*Removed during processing

In a separate container, Poloxamer® 188 [BASF] was dissolved in purified water (poloxamer solution). Sugar, sodium citrate, anhydrous citric acid, sodium benzoate, and sucralose were added into high shear granulator and granulation process was performed using Poloxamer solution. Wet granules were dried using fluid bed drier until moisture level was below 1.50%. Dried granules were then milled through Fitz mill equipped with 20 mesh screen (openings of about 850 µm). This was the Diluent Granules.

E. Methylphenidate ER Powder Blend

| Ingredient | Quantity |
|---|---|
| Diluent Granules | 34066 g |
| Starch | 3134 g |
| Xanthan gum | 341 g |
| Talc | 455 g |
| Banana flavor | 341 g |
| Silicon dioxide | 455 g |
| Sugar | 1359 g |
| Coated Methylphenidate - Ion exchange Resin Complex - Matrix | 4499 g |
| Uncoated Methylphenidate - Ion Exchange Resin Complex | 770 g |

Diluent granules prepared according to Part D were loaded in to a 'V' blender. Starch, xanthan gum, talc, banana flavor, silicon dioxide, sugar, coated methylphenidate-ion exchange resin complex-matrix prepared according to Part C, and uncoated Methylphenidate-ion exchange resin complex prepared as described in Part A (weight ratio of approximately 80 parts by weight coated to approximately 20% parts by weight uncoated methylphenidate-ion exchange resin complex, based on the weight ratio of the methylphenidate in each component) were loaded into a 'V' blender and mixed for 10 minutes.

Following mixing, the blend of the uncoated Methylphenidate-ion exchange resin complex and coated methylphenidate-ion exchange resin complex-matrix (Polistirex ER Powder blend) was filled into an appropriate container which, when reconstituted with purified water, achieved a concentration equivalent to 25 mg methylphenidate hydrochloride per 5 mL. When water is added, the resulting oral liquid suspension has a pH in the range of about 4.2.

In an initial study, the pharmacokinetic parameters of the 25 mg methylphenidate/5 mL suspension formulation of this example were studied from 0 to 24 hours. The mean plasma d-methylphenidate concentration is shown in FIG. 1. This formulation was administered as a single oral dose of 72 mg, and compared to a commercially available solid extended release methylphenidate formulation (Concerta®, administered as a 72 mg dose (four 18 mg tablets). The mean $T_{max}$ for this formulation is 3.77 hours.

Summary of Methylphenidate Pharmacokinetic Parameters

| | Geometric Mean | | T/R Ratio | 90% Confidence Limits | | Intra-Subj |
|---|---|---|---|---|---|---|
| MPH | TEST | Ref | (%) | Lower | Upper | CV (%) |
| $C_{max}$ (ng/mL) | 17.02 | 17.36 | 98.03 | 90.73 | 105.92 | 9.89 |
| $AUC_{(0-t)}$ (ng·h/mL) | 160.13 | 182.90 | 87.55 | 82.44 | 92.98 | 7.67 |
| $AUC_{(0-\infty)}$ (ng·h/mL) | 171.50 | 188.54 | 90.96 | 85.38 | 96.92 | 8.09 |
| $AUC_{pR}$ (ng·h/mL) | 91.50 | 188.54 | 127.24 | 119.20 | 135.82 | 8.33 |

AUCpR is the area under the curve to the population median Tmax of the reference formulation.
$AUC_{0-t}$ is the area under the plasma/serum/blood concentration-time curve from time zero to time t, where t is the last time point with measurable concentration for individual formulation.
T/R ratio refers to the test formulation (methylphenidate polistirex 25 mg/5 mL ER oral suspension) to reference (R) formulation.
Intra-subject CV % refers to the geometric (CV) coefficient of variation between subjects.

The average peak plasma concentration from a single oral dose under fasting conditions is reached in 2 to 5 hours. The 12-hour plasma concentration was 5 ng/mL. Based on the pharmacokinetic study, rapid onset of action was observed at the first measured time point (45 minutes) and an extended release profile (i.e., about 12 hours) was observed in adult ADHD patients.

F. Chemical Stability

The chemical stability of the methylphenidate ER powder of the invention, prepared as described in this Example, following admixing in water at the varying concentrations shown in the table below to form a suspension have a pH of 4.2 was assessed. The resulting Methylphenidate ER suspension shows that the resulting product maintains about 98% of its initial potency with its primary degradant (theo-α-phenyl-1-piperidineacetic acid hydrochloride) of not more than 0.7% after 4 months of storage of the reconstituted powder blend at ambient condition. The chemical stability data is show in the following table.

| Condition | % Potency | % Impurity* |
|---|---|---|
| Initial | 99 | 0.1 |
| 2 months | 99 | 0.4 |
| 3 months | 98 | 0.7 |
| 4 months | 97 | 0.7 |

*Theo-α-phenyl-2-piperidineacetic acid hydrochloride

These results show that the composition of increase in impurities is not directly linked to loss of potency.

Example 2

Methylphenidate ER Powder for Aqueous Oral Suspension

Example 2 illustrates preparation of an oral suspension composition reconstituted from a methylphenidate (MPH) extended release (ER) powder for oral suspension. In this example, the MPH ER powder blend is a combination of (i) an uncoated methylphenidate-ion exchange resin, (ii) a cured, coated (polyvinylacetate-plasticizer, 45% weight gain) methylphenidate-ion exchange resin complex-hydrophilic polymer matrix, and (iii) diluent granules.

A. Uncoated Methylphenidate-Ion Exchange Resin Complex

| Ingredients | Quantity |
|---|---|
| Methylphenidate HCl | 100 g |
| Amberlite ® IRP69 Sodium Polystyrene Sulfonate Resin | 235.75 g |
| Purified Water* | Qs* |

*Removed during processing

The methylphenidate-ion exchange resin complex was prepared by first adding 2 L of purified water into the vessel and dissolving methylphenidate HCl in the water by continuous mixing. The Amberlite® IRP69 sodium polystyrene sulfonate resin was dispersed into the solution with continuous mixing, which was continued for 120 minutes. Water was removed by filtration process followed by rinsing twice using purified water. The wet resin complex was then dried until the moisture content was 3 to 7%. This dried methylphenidate-ion exchange resin complex was passed through a CO-MIL device fitted with a standard 40 mesh screen. This was the particulate uncoated Methylphenidate-ion exchange resin (methylphenidate polistirex).

B. Precoated Methylphenidate-Ion Exchange Resin Complex-Matrix

| Ingredients | Quantity |
|---|---|
| Methylphenidate HCl | 650 g |
| Amberlite IRP 69 Sodium Polystyrene Sulfonate Resin | 1613.03 g |
| Purified Water* | Qs* |
| Kollidon ® K30 | 547.09 g |
| Purified water* | 182 g |
| Purified Water* | Qs* |

*Removed during processing

A methylphenidate-ion exchange resin complex was prepared by first adding 10 L of Purified Water into the vessel and adding in methylphenidate HCl which was dissolved by continuous mixing. Sodium Polystyrene Sulfonate resin [Amberlite IRP69, Rohm & Haas] was dispersed into the solution with continuous mixing, which was continued for 60 minutes. Water was removed by filtration process followed by rinsing twice using purified water. Wet resin complex was then dried until moisture content was to 25%. In a separate container Kollidon® K30 (BASF) was dissolved in 547.09 gms of Purified Water (PVP solution). The partially dried methylphenidate-ion exchange resin complex was treated with the PVP solution with continuous mixing to form a uniform wet mass of the methylphenidate-ion exchange resin-PVP matrix. The uniform wet mass was dried until the moisture content was 15 to 25%. Semi-dried methylphenidate-ion exchange resin complex-matrix was then passed through a CO-MIL™ device fitted with a standard 40 mesh screen. Milled methylphenidate-ion exchange resin matrix was further dried until moisture content was 3 to 7%. Dried material was again passed through a CO-MIL™ device fitted with a standard 40 mesh screen. This was the particulate precoated methylphenidate-ion exchange resin matrix.

C. Coated Methylphenidate-Ion Exchange Resin Complex-Matrix

| Ingredients | Quantity |
|---|---|
| Precoated methylphenidate - ion exchange resin complex - matrix (from Part B) | 600 g |
| Kollicoat ® SR30D** | 952.35 g |
| Triacetin | 14.25 g |
| Purified Water* | 533.4 g |

*Removed during processing
**30% w/w aqueous dispersion

The precoated methylphenidate-ion exchange resin complex-matrix was coated as follows. The coating solution was prepared by mixing triacetin, purified water and the Kollicoat® SR30D polyvinyl acetate dispersion (BASF) in a separate container. The coating process was performed in a fluid bed processor equipped with Wurster column by applying coating solution onto precoated methylphenidate-ion exchange resin complex-matrix prepared according to Part B that resulted in 45% weight gain. The (Kollicoat® SR30D—triacetin) coated methylphenidate-ion exchange resin complex-matrix was cured in a hot air oven at 60° C. for 5 hours. The cured coated methylphenidate-ion exchange resin complex-matrix was passed through a standard 40 mesh screen.

D. Diluent Granules

| Ingredient | Quantity |
| --- | --- |
| Poloxamer 188 | 2.25 g |
| Purified water* | 50 g |
| Sugar | 625.97 g |
| Sodium citrate | 17.38 g |
| Anhydrous citric acid | 23.22 g |
| Sodium benzoate | 9 g |

*Removed during processing

In a separate container, the Poloxamer 188 was dissolved in purified water (poloxamer solution). Sugar, sodium citrate, anhydrous citric acid, and sodium benzoate were added into a high shear granulator and a granulation process was performed using the Poloxamer solution. Wet granules were dried using fluid bed drier until moisture level was below 1.5%. Dried granules were then milled through a Fitz mill equipped with 20 mesh screen to form the Diluent Granules.

E. Methylphenidate ER Powder Blend

| Ingredient | Quantity |
| --- | --- |
| Diluent Granules | 37.16 g |
| Starch | 5.716 g |
| Xanthan Gum | 0.628 g |
| Coated Methylphenidate - Ion Exchange Resin Complex - Matrix | 6.073 g |
| Uncoated Methylphenidate - Ion Exchange Resin Complex | 0.424 g |

Diluent Granules prepared according to Part D were mixed with starch, xanthan gum, coated methylphenidate-ion exchange resin complex-matrix prepared as described in part C of this Example, and Uncoated Methylphenidate-Ion Exchange Resin Complex prepared as described in Part A of this example. The powder blend contained a weight ratio of about 90% by weight methylphenidate in sustained release form (coated complex-matrix) to about 10% by weight methylphenidate in immediate release form (uncoated methylphenidate-ion exchange resin complex), based upon the total weight of the methylphenidate in the formulation.

The Methylphenidate ER Powder blend was filled into an appropriate container which, when reconstituted with purified water, achieved a concentration equivalent to 25 mg methylphenidate hydrochloride per 5 mL.

Example 3

Methylphenidate ER Powder for Aqueous Oral Suspension

In this example, the MPH ER powder blend is a combination of (i) an uncoated methylphenidate-ion exchange resin, (ii) a cured, barrier coated (polyvinylacetate-plasticizer, 35% weight gain) methylphenidate-ion exchange resin complex-hydrophobic polymer matrix, and (iii) diluent granules.

A. Uncoated Methylphenidate-Ion Exchange Resin Complex

| Ingredients | Quantity |
| --- | --- |
| Methylphenidate HCl | 100 g |
| Amberlite ® IRP69 Sodium Polystyrene Sulfonate Resin | 248.2 g |
| Purified Water* | Qs* |

*Removed during processing

The methylphenidate-ion exchange resin complex was prepared by first adding 1.5 L of purified water into the vessel and dissolving methylphenidate HCl therein by continuous mixing. Amberlite® IRP69 ion exchange resin was dispersed into the solution with continuous mixing, which mixing was continued for 60 minutes. Water was removed by filtration process followed by rinsing twice using purified water. The wet resin complex was then dried until moisture content was 3% to 7%. Dried drug-resin complex was passed through a CO-MIL device fitted with a standard 40 mesh screen. This was the particulate uncoated Methylphenidate-ion exchange resin complex.

B. Precoated Methylphenidate Ion Exchange Resin Complex-Matrix

| Ingredients | Quantity |
| --- | --- |
| Methylphenidate HCl | 650 g |
| Amberlite ® IRP 69 Sodium Polystyrene Sulfonate Resin | 1613.03 g |
| Purified Water* | Qs* |
| Kollicoat ® SR 30D** | 606.7 g |
| Purified water* | 505 g |
| Purified Water* | Qs* |

*Removed during processing
**30% w/w aqueous dispersion

A methylphenidate-ion exchange resin complex was prepared by first adding 10 L of Purified Water in to the vessel and dissolving methylphenidate HCl therein by continuous mixing. Amberlite® IRP69 was dispersed in the solution with continuous mixing, which was continued for 60 minutes. Water was removed by filtration process followed by rinsing twice using purified water. Wet resin complex was then dried until moisture content was 15% to 20%. In a separate container Kollicoat® SR 30D [27% Polyvinylacetate, 2.7% polyvinylpyrrolidone, 0.3% sodium lauryl sulfate] was mixed with 505 gms of purified water (Kollicoat Dispersion). The partially dried resin complex was combined with the Kollicoat Dispersion with continuous mixing to form a uniform wet mass of the methylphenidate-ion exchange resin complex-Kollicoat® SR30D matrix. The wet mass was dried until the moisture content was 10% to 15%. Semi-dried methylphenidate-ion exchange resin complex-matrix was then passed through a CO-MIL device mill fitted with a standard 40 mesh screen. The milled methylphenidate-ion exchange resin complex-matrix was further dried until moisture content was 3% to 7%. Dried methylphenidate-ion exchange resin complex-matrix was passed through a CO-MIL fitted with a standard 40 mesh screen. This was the precoated methylphenidate-ion exchange resin complex-matrix.

C. Coated Methylphenidate-Ion Exchange Resin Complex-Matrix

| Ingredients | Quantity |
| --- | --- |
| Precoated Methylphenidate - Ion Exchange Resin Complex - Matrix (from Part B) | 600 g |
| Kollicoat ® SR30D** | 761.88 g |
| Triacetin | 11.40 g |
| Purified Water* | 426.72 g |

*Removed during processing
**30% w/w aqueous dispersion

The precoated methylphenidate-ion exchange resin complex-matrix was coated as follows. The coating solution was prepared by mixing triacetin, purified water and Kollicoat® SR30D (aqueous dispersion, 30% solids) in a separate container. The coating process was performed in a fluid bed processor equipped with Wurster column by applying coating solution onto precoated methylphenidate-ion exchange resin complex-matrix of part B that resulted in 35% weight gain. The coated methylphenidate-ion exchange resin complex-matrix was cured in a hot air oven at 60° C. for 5 hours. The cured coated Methylphenidate-ion exchange resin complex-matrix was again passed through a standard 40 mesh screen.

D. Diluent Granules

| Ingredient | Quantity |
| --- | --- |
| Poloxamer ® 188 | 2.25 g |
| Purified water* | 50 g |
| Sugar | 625.97 g |
| Sodium citrate | 17.38 g |
| Anhydrous citric acid | 23.22 g |
| Sodium benzoate | 9 g |

*Removed during processing

In a separate container, Poloxamer™ was dissolved in purified water (poloxamer solution). Sugar, sodium citrate, anhydrous citric acid, and sodium benzoate were added into a high shear granulator and a granulation process was performed using the Poloxamer solution. Wet granules were dried using fluid bed drier until moisture level was below 1.5%. Dried granules were then milled through Fitz mill equipped with 20 mesh screen. This was the Diluent Granules.

E. Methylphenidate ER Powder Blend

| Ingredient | Quantity |
| --- | --- |
| Diluent Granules | 75.45 g |
| Starch | 11.43 g |
| Xanthan Gum | 1.256 g |
| Coated Methylphenidate - Ion Exchange Resin Complex - Matrix | 10.144 g |
| Uncoated Methylphenidate - Ion Exchange Resin Complex | 1.724 g |

Diluent granules prepared as described in Part D were mixed with starch, xanthan gum, coated methylphenidate-ion exchange resin complex-matrix prepared as described in Part C and uncoated Methylphenidate-Ion Exchange Resin Complex prepared as described in Part A. The ratio of immediate release methylphenidate (uncoated complex) and sustained release methylphenidate (coated complex-matrix) was 10 parts by weight immediate release methylphenidate to 90 parts by weight sustained release methylphenidate, based on the total weight of methylphenidate in the formulation. The Methylphenidate Polistirex ER Powder blend was filled into an appropriate container which, when reconstituted with purified water, achieved a concentration equivalent to 25 mg methylphenidate hydrochloride per 5 mL.

Example 4

Methylphenidate ER Powder for Aqueous Oral Suspension

In this example, the MPH ER powder is a combination of (i) an uncoated methylphenidate-ion exchange resin (immediate release MPH component), (ii) a cured, coated (ethylcellulose, 30% weight gain) methylphenidate-ion exchange resin complex-hydrophilic polymer matrix (sustained release MPH component), and (iii) diluent granules.

A. Uncoated Methylphenidate-Ion Exchange Resin Complex

| Ingredients | Quantity |
| --- | --- |
| Methylphenidate HCl | 3100 g |
| Amberlite ® IRP69 Sodium Polystyrene Sulfonate Resin | 7693 g |
| Purified Water* | Qs* |

*Removed during processing

The methylphenidate-ion exchange resin complex was prepared by first adding 80 L of Purified Water in to the vessel and methylphenidate HCl was dissolved therein by continuous mixing. Amberlite™ IRP69 ion exchange resin was dispersed with continuous mixing, which mixing was continued for 60 minutes. Water was removed by filtration process followed by rinsing twice using purified water (40 L). The wet methylphenidate-ion exchange resin complex was then dried until moisture content was 3 to 7%. Dried methylphenidate-ion exchange resin complex was passed through the CO-MIL device fitted with a standard 40 mesh screen. This was the Uncoated Methylphenidate-ion exchange resin complex.

B. Precoated Methylphenidate-Ion Exchange Resin Complex-Matrix

| Ingredients | Quantity |
| --- | --- |
| Uncoated Methylphenidate - Ion Exchange Resin Complex (From Part A) | 8500 g |
| Kollidon ® K30 | 657 g |
| Purified water* | 2629 g |
| Purified Water* | Qs* |

*Removed during processing

In a separate container Kollidon K30 was dissolved in 2629 gms of Purified Water (PVP solution). Uncoated Methylphenidate-ion exchange resin complex prepared as described in Part A was treated with the PVP solution until a 7.73% polymer weight gain was achieved and with continuous mixing to form a uniform mass. Wet mass was dried until the moisture content was 15% to 25%. Semi-dried material was then milled using a CO-MIL device fitted with a standard 40 mesh screen. Milled material was further dried until moisture content was 3 to 7%. Dried material was again passed through a CO-MIL device fitted with a standard 40 mesh screen. This was the precoated methylphenidate ion exchange resin complex-matrix.

C. Coated Methylphenidate-Ion Exchange Resin Complex-Matrix

| Ingredients | Quantity |
| --- | --- |
| Precoated Methylphenidate - Ion Exchange Resin Complex Matrix (From Part B) | 600 g |
| Surelease ® ethylcellulose dispersion | 780 g |
| Purified Water* | 520 g |

*Removed on processing
**28% w/w aqueous dispersion

The precoated methylphenidate-ion exchange resin complex-matrix was coated as follows. The coating solution was prepared by mixing purified water and Surelease™ in a separate container. Surelease™ is available from Colorcon as an aqueous ethyl cellulose dispersion containing water (70.6% w/w), ethylcellulose (18.8% w/w), ammonium hydroxide (4.4% w/w), a medium chain triglyceride (4.0% w/w), and oleic acid (2.2% w/w), with a viscosity of 20 cps. The coating process was performed in a fluid bed processor equipped with Wurster column by applying coating solution on to the precoated Methylphenidate ion exchange resin complex-matrix prepared as described in Part B above that resulted in 30% weight gain. The coated Methylphenidate ion exchange resin complex-matrix was cured in a hot air oven at 60° C. for 5 hours. The cured coated Methylphenidate-ion exchange resin complex-matrix was again passed through a standard 40 mesh screen.

C. Diluent Granules

| Ingredient | Quantity |
| --- | --- |
| Poloxamer ™ 188 | 30 g |
| Purified water* | 600 g |
| Sugar | 8260.63 g |
| Sodium citrate | 231.76 g |
| Anhydrous citric acid | 309.6 g |
| Sodium benzoate | 120 g |
| Sucralose | 48 g |

*Removed during processing

In a separate container, the surfactant was dissolved in purified water (poloxamer solution). Sugar, sodium citrate, anhydrous citric acid, sodium benzoate, and sucralose were added into a high shear granulator and granulation was performed using the Poloxamer solution. Wet granules were dried using fluid bed drier until moisture level was below 1.50%. Dried granules were then milled through Fitz mill equipped with 20 mesh screen. This was the Diluent Granules.

E. Methylphenidate ER Powder Blend

| Ingredient | Quantity |
| --- | --- |
| Diluent Granules | 480 g |
| Starch | 44.16 g |
| Xanthan gum | 4.8 g |
| Talc | 6.4 g |
| Banana flavor | 4.8 g |
| Silicon dioxide | 6.4 g |
| Sugar | 19.46 g |
| Coated Methylphenidate Ion Exchange Resin Complex - Matrix | 62.78 g |
| Uncoated Methylphenidate - Ion Exchange Resin Complex | 11.2 g |

The Diluent granules of Part D above were loaded in to a 'V' blender. Starch, xanthan gum, talc, banana flavor, silicon dioxide, sugar, coated methylphenidate-ion Exchange Resin complex-matrix prepared as described in Part C, and Uncoated Methylphenidate-Ion Exchange Resin Complex prepared as described in Part A of this Example, were loaded into the 'V' blender and mixed for 10 minutes. The resulting blend contained 80 parts by weight of sustained release MPH (coated matrix) to 20 parts by weight immediate release MPH (uncoated complex), based on the total weight of MPH in the final ER powder blend formulation. The Methylphenidate ER Powder blend was filled into an appropriate container which, when reconstituted with purified water, achieved a concentration equivalent to 25 mg methylphenidate hydrochloride per 5 mL.

Example 5

Methylphenidate ER Powder for Aqueous Oral Suspension

In this example, the MPH ER powder is a combination of (i) an uncoated methylphenidate-ion exchange resin, (ii) a coated (Eudragit RS/RL polyacrylate based coat, 30% weight gain) methylphenidate-ion exchange resin complex-hydrophilic polymer matrix, and (iii) diluent granules.

A. Uncoated Methylphenidate-Ion Exchange Resin Complex

| Ingredients | Quantity |
| --- | --- |
| Methylphenidate HCl | 3100 g |
| Amberlite ® IRP69 Sodium Polystyrene Sulfonate Resin | 7693 g |
| Purified Water* | Qs* |

*Removed during processing

The methylphenidate-ion exchange resin complex was prepared by first adding 80 L of purified water into the vessel and methylphenidate HCl was dissolved therein by continuous mixing. Amberlite® IRP69 ion exchange resin was dispersed in the solution with continuous mixing, which mixing was continued for 60 minutes. Water was removed by filtration process followed by rinsing twice using purified water (40 L). Wet methylphenidate-ion exchange resin complex was then dried until the moisture content was 3% to 7%. Dried methylphenidate-ion exchange resin complex was passed through a CO-MIL device fitted with a standard 40 mesh screen. This was the uncoated Methylphenidate-ion exchange resin complex.

B. Precoated Methylphenidate-Ion Exchange Resin Complex-Matrix

| Ingredients | Quantity |
| --- | --- |
| Uncoated Methylphenidate - Ion Exchange Resin Complex (from Part A) | 8500 g |
| Kollidon ® K30 | 657 g |
| Purified water* | 2629 g |
| Purified Water* | Qs* |

*Removed during processing

In a separate container the PVP was dissolved in 2629 gms of purified water (Povidone solution). Uncoated Methylphenidate-ion exchange resin complex prepared as described in A was mixed with the Povidone solution until a polymer weight gain of 7.73% was achieved, with continuous mixing to form a uniform mass of precoated methylphenidate-ion exchange resin-PVP matrix. Wet mass was dried until the moisture content was 15% to 25%. Semi-dried material was then passed through a CO-MIL device fitted with a standard 40 mesh screen. Milled methylphenidate-ion exchange resin matrix was further dried until moisture content was 3% to 7%. Dried methylphenidate-ion exchange resin matrix was passed through a CO-MIL device fitted with a standard 40 mesh screen. This was the precoated Methylphenidate-ion exchange resin complex-matrix.

C. Coated Methylphenidate Ion Exchange Resin Complex-Matrix

| Ingredient | Quantity |
| --- | --- |
| Precoated Methylphenidate - Ion Exchange Resin Complex - Matrix (From Part B) | 600 g |
| Eudragit ™ RS** | 376.30 g |
| Eudragit ™ RL** | 75.26 g |
| Triethyl citrate | 27 g |
| Talc | 33.87 g |
| Purified Water* | 694.56 g |

*Removed during processing
**(30% w/w aqueous dispersion)

The precoated methylphenidate-ion exchange resin complex matrix was coated as follows. The coating solution was prepared by dispersing triethyl citrate and talc in purified water using a high shear mixer (Talc dispersion). In a separate container Eudragit™ dispersion was prepared by mixing Eudragit™ RS 30D [a pH-independent, 30% aqueous dispersion of poly(ethyl acrylate-co-methyl methacrylate-co-trimethylammonioethyl methacrylate chloride) 1:2:0.1)] and Eudragit™ RL 30D [a 30% aqueous dispersion, pH independent polymer, poly(ethyl acrylate-co-methyl methacrylate-co-trimethylammonioethyl methacrylate chloride) 1:2:0.2)]. The Talc dispersion was mixed with the Eudragit™ RS/RL dispersion. The coating process was performed in a fluid bed processor equipped with Wurster column by applying coating solution onto the precoated Methylphenidate-ion exchange resin complex-matrix from Part B until in 30% weight gain was achieved. The coated Methylphenidate-ion exchange resin complex-matrix was passed through Sieve No. 40 mesh screen after coating. No curing at elevated temperature was performed.

D. Diluent Granules

| Ingredient | Quantity |
| --- | --- |
| Poloxamer ™ 188 | 30 g |
| Purified water* | 600 g |
| Sugar | 8260.63 g |
| Sodium citrate | 231.76 g |
| Anhydrous citric acid | 309.6 g |
| Sodium benzoate | 120 g |
| Sucralose | 48 g |

*Removed during processing

In a separate container, Poloxamer surfactant was dissolved in purified water (poloxamer solution). Sugar, sodium citrate, anhydrous citric acid, sodium benzoate, and sucralose were added into high shear granulator and granulation process was performed using Poloxamer solution. Wet granules were dried using fluid bed drier until moisture level was below 1.50%. Dried granules were then milled through Fitz mill equipped with 20 mesh screen. This was the Diluent Granules.

E. Methylphenidate ER Powder Blend

| Ingredient | Quantity |
| --- | --- |
| Diluent Granules (Part D) | 480 g |
| Starch | 44.16 g |
| Xanthan gum | 4.8 g |
| Talc | 6.4 g |
| Banana flavor | 4.8 g |
| Silicon dioxide | 6.4 g |
| Sugar | 16.44 g |
| Coated Methylphenidate - Ion exchange resin complex - matrix | 65.72 g |
| Uncoated Methylphenidate - Ion exchange resin complex | 11.23 g |

Diluent granules prepared as in Part D were loaded in to a 'V' blender. Starch, Xanthan gum, Talc, Banana flavor, Silicon dioxide, Sugar, coated Methylphenidate-ion exchange resin complex matrix prepared as in Part C, and Uncoated Methylphenidate ion exchange resin complex prepared as described in Part A were loaded into the 'V' blender and mixed for 10 minutes. The resulting methylphenidate ER powder blend contained a ratio of 80 parts by weight MPH in sustained release form (coated methylphenidate ion exchange resin complex matrix) to 20 parts by weight MPH in immediate release form (uncoated MPH ion exchange resin complex), based on the total weight of MPH in the MPH ER powder blend.

The Methylphenidate ER Powder blend was filled into an appropriate container which, when reconstituted with purified water, achieved a concentration equivalent to 25 mg methylphenidate hydrochloride per 5 mL.

Example 6 pH-Chemical Stability of Methylphenidate Extended Release Powder Blend in an Aqueous Oral Suspension, 25 mg/5 mL Methylphenidate shows pH-dependent stability in aqueous media, and its primary degradant, threo-α-phenyl-2-piperidineacetic acid, is primarily generated through hydrolysis. A pH stability study was conducted on suspensions based on the reconstituted methylphenidate ER powder blend prepared as described in Example 1 [Methylphenidate-ion exchange resin complex prepared as described in Example 1, Part A (weight ratio of approximately 80 parts by weight coated to approximately 20% parts by weight uncoated methylphenidate-ion exchange resin complex in Example 1, based on the weight ratio of the methylphenidate in each component) were loaded into a 'V' blender and mixed for 10 minutes. The methylphenidate ER powder blend for suspension was added with purified water to yield a suspension containing methylphenidate equivalent to 25 mg per 5 mL methylphenidate hydrochloride.

The aqueous suspension containing the methylphenidate extended release powder blend of Example 1 was adjusted with either HCl or NaOH to obtain various samples with different pHs ranging from 2 to 6. The samples were placed at 40° C./75% RH (relative humidity) for 1 month and tested for their potency and impurity. The stability of the suspension was assessed based on the percent (%) potency remaining when compared to the initial potency of the suspension and its primary degradant, threo-α-phenyl-2-piperidineacetic acid.

Figure 2:
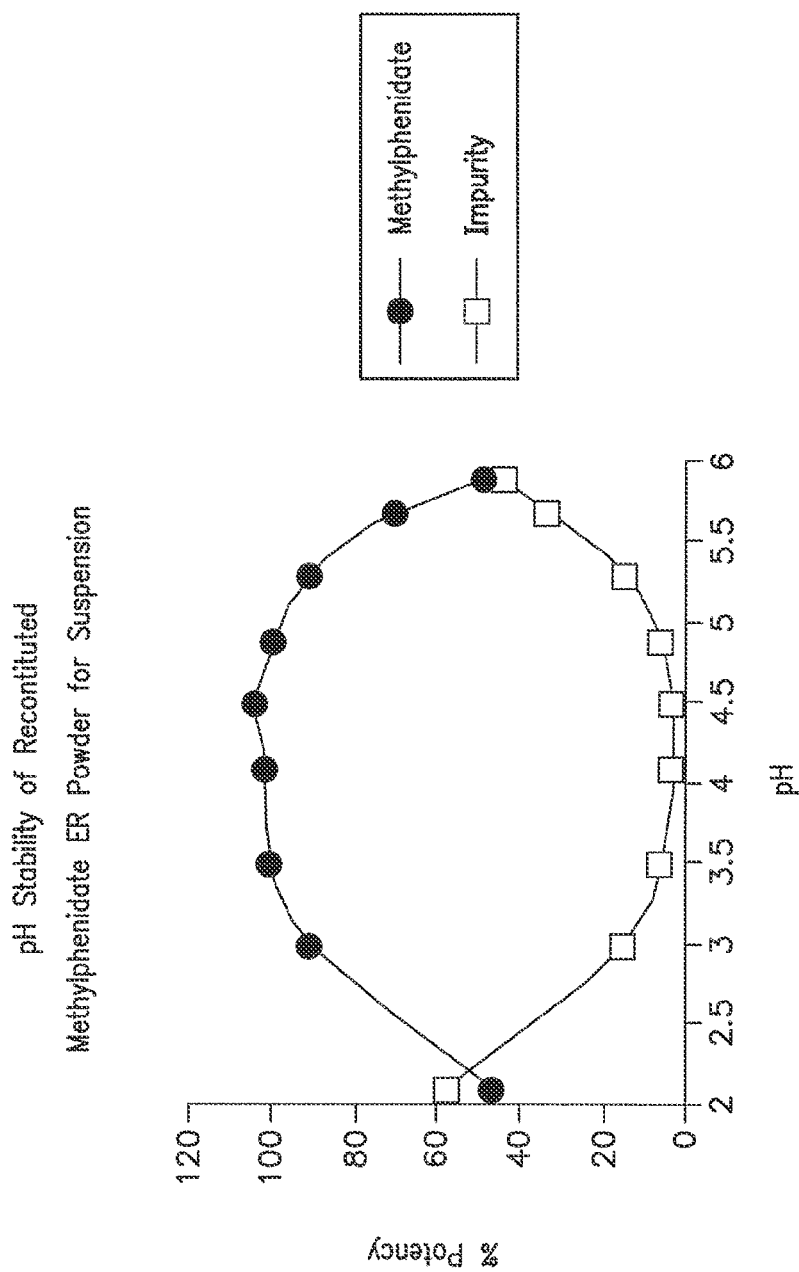
FIG. 2 illustrates the pH-Chemical Stability of Reconstituted Methylphenidate-Ion Exchange Resin Powder for Oral Suspension, 25 mg/5 mL, as described in Example 6.

The results are provided in the following table and FIG. 2.

| pH | % Potency @ 1 month | % Impurity* |
|---|---|---|
| 2.1 | 44.5 | 57.2 |
| 3.0 | 89.1 | 15.0 |
| 3.5 | 98.4 | 5.6 |
| 4.1 | 96.5 | 2.7 |
| 4.5 | 101.2 | 2.9 |
| 4.9 | 95.9 | 6.2 |
| 5.3 | 88.9 | 15.1 |
| 5.7 | 66.5 | 33.4 |
| 5.9 | 46.6 | 43.1 |

*impurity: Threo-α-Phenyl-2-piperidineacetic Acid

These results show the product is most stable at pH between 3.5 and 5.0, and becomes less stable when pH is above 5.0 or below 3.5. It is noted that there is no direct correlation between the percentage of the impurity and loss of potency.

Example 7

Single Dose Pharmacokinetics of an Extended Release Methylphenidate Suspension

To determine the single-dose pharmacokinetics of an aqueous suspension formulation, the MPH ER powder blend of Example 1 was combined with water to achieve a concentration of about 25 mg/5 mL and the resulting suspension was dosed at an amount equivalent to 60 mg racemic methylphenidate HCl. This suspension was compared with two doses of a commercially available 30 mg immediate release liquid MPH (Methylin®, reference immediate release (IR) MPH), which was dosed at hours 0 and 6 in adults.

The following results show that a single dose of a 60 mg aqueous suspension formulation of the invention is bioequivalent to two 30-mg doses of reference IR MPH, and the 60 mg aqueous suspension formulation of the invention has a lower peak plasma concentration than the reference IR MPH product.

30 healthy subjects aged 18 to 68 years (25 men, 5 women, mean 36.5 years) were enrolled in this open-label, crossover study and randomly assigned to receive the 60 mg methylphenidate aqueous suspension formulation of the invention or the reference IR MPH after an overnight fast. Blood samples were collected prior to dose at hour 0 and at post-dose hours 0.5, 1, 1.33, 1.67, 2, 2.5, 3, 4, 5, 6, 6.5, 7, 7.33, 7.67, 8, 9.5, 9, 10, 12, 14, 16, 24 and 36. Plasma concentrations of d- and l-MPH were determined and pharmacokinetic parameters were calculated. Twenty-eight subjects completed the study.

A. Pharmacokinetics

Figure 3:
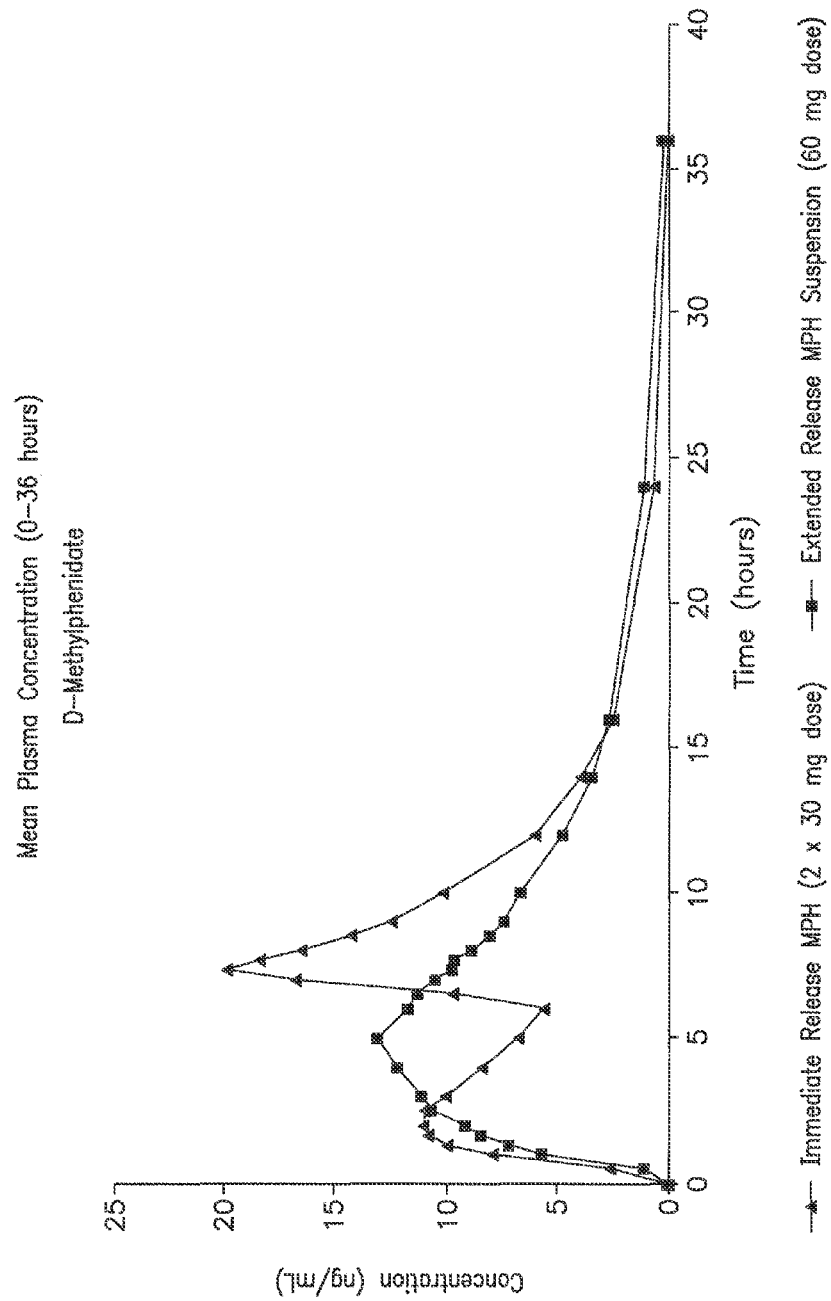
FIG. 3 provides the pK profile of an oral aqueous extended release formulation of the invention containing the methylphenidate ER powder blend of Example 1 suspended in water to form an aqueous methylphenidate liquid suspension formulation having a concentration of 25 mg per 5 mL, which formulation provides both an immediate release and an extended release profile. For this study (see Example 7A), the oral aqueous liquid extended release formulation was dosed to provide an amount of methylphenidate equivalent to a 60 mg dose of methylphenidate HCl.

The pharmacokinetic profile is provided in FIG. 3. Following administration of the 60 mg aqueous oral suspension formulation of the invention, the mean plasma d-MPH concentration increased rapidly for about 1 hour and then continued to a slower increase until peaking at 5 hours, after which a gradual decline in plasma concentration was observed. See FIG. 3.

| Summary of d-Methylphenidate Mean Pharmacokinetic Parameters | | |
|---|---|---|
| Parameters | 60 mg Test (n = 28) | IR MPH Reference (n = 28) |
| $AUC_{0-\infty}$ | 143.65 (50.67) | 151.31 (54.84) |
| $C_{max}$ (ng/mL) | 13.61 (42.56) | 20.94 (61.89) |
| $T_{max}$ (hr) | 5.00 (1.67-6.00) | 7.33 (6.5-8.00) |
| $T_{1/2}$ (hr) | 5.65 (15.01) | 3.74 (16.29) |

$T_{1/2}$—Terminal phase elimination half life
$T_{max}$—Time to peak (maximum) observed plasma drug concentration
$C_{max}$—Peak (maximum) observed plasma drug concentration
$AUC_{0-\infty}$—Area under the concentration - time curve from time zero to infinity The results for $AUC_{0-\infty}$, $C_{max}$, and $T_{1/2}$ are presented as geometric mean (percent coefficient of variation) and results for $T_{max}$ presented as median (range).

The $AUC_{0-\infty}$ of d-MPH for the aqueous suspension of the invention and reference IR MPH were 143.65 and 153.31 ng-hr/mL, respectively.

B. Absorption

Figure 4:
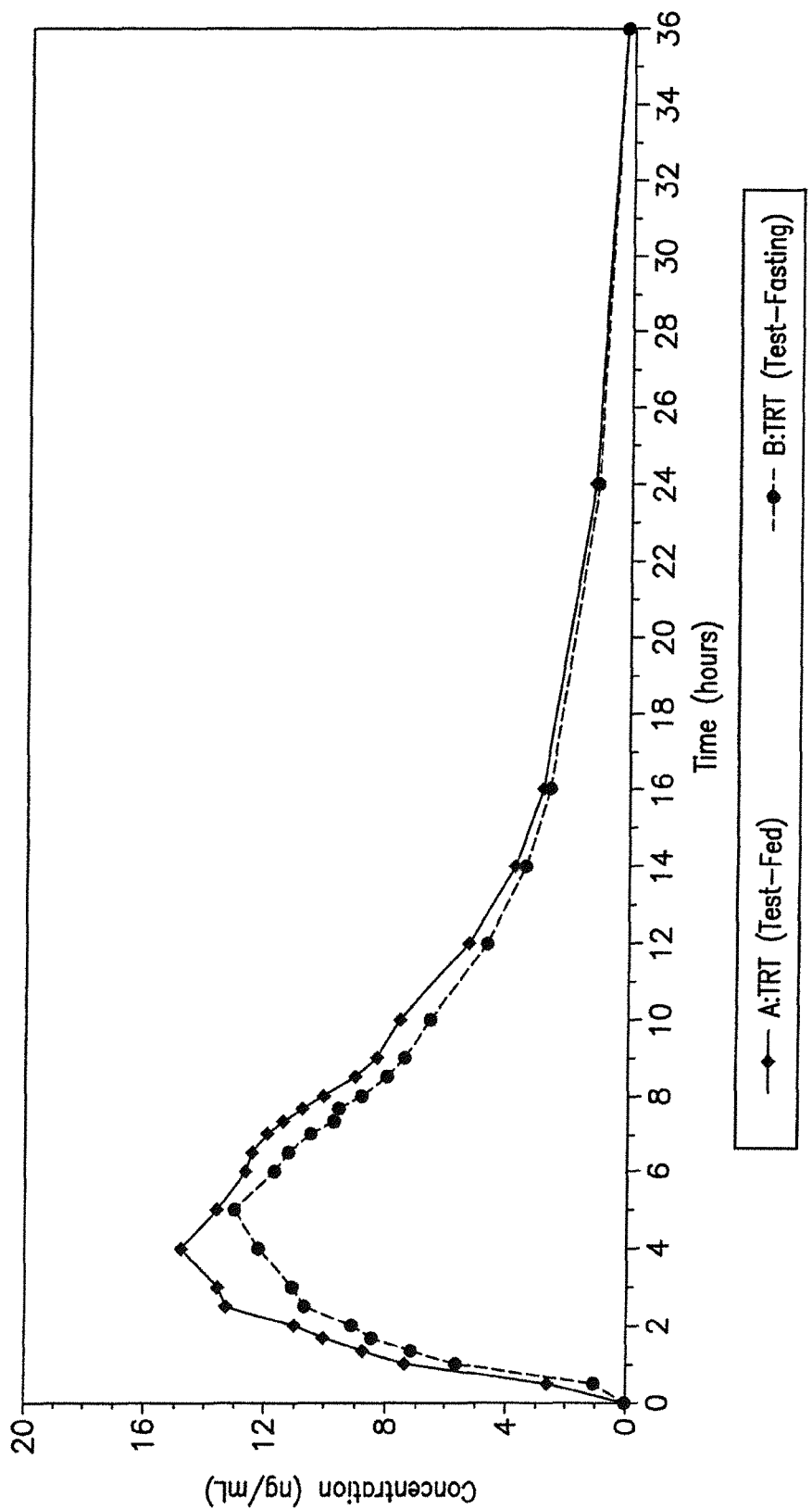
FIG. 4 provides the results of an absorption study (Example 7B), illustrated by the mean d-Methylphenidate plasma concentrations against time of an oral aqueous extended release formulation of the invention equivalent to a 60-mg methylphenidate HCl dose under fed (A, n=27) and fasting (B, n=28) conditions.

Following a single, 60 mg oral dose of the MPH extended release suspension prepared as in Example 1, in 28 healthy adult subjects under fasting conditions, d-methylphenidate mean (±SD) peak plasma concentrations ($C_{max}$) of 13.6 (±5.8) ng/mL occurred at a median time of 5.0 hours after dosing. The $C_{max}$ (ng/mL) was 20.94 for the reference IR MPH product. The results are illustrated in FIG. 4.

C. Metabolism and Excretion

Following a single 60 mg oral dose of the MPH extended release liquid suspension prepared as in Example 1 in 28 healthy adult subjects under fasting conditions, the mean plasma terminal elimination half-life of d-methylphenidate was 5.6 (±0.8) hours and $T_{max}$ was 5 hours. For the reference IR MPH, the half-life was 3.74 hours and $T_{max}$ was 7.33 hours.

In humans, methylphenidate is metabolized primarily via deesterification to alpha-phenyl-piperidine acetic acid (PPAA). The metabolite has little or no pharmacologic activity.

After oral dosing of radiolabeled methylphenidate in humans, about 90% of the radioactivity was recovered in urine. The main urinary metabolite was PPAA, accounting for approximately 80% of the dose.

D. Food Effects

In a study in adult volunteers to investigate the effects of a high-fat meal on the bioavailability of the methylphenidate at a dose of 60 mg, the presence of food reduced the time to peak concentration by approximately 1 hour (5 hours, fasted and 4 hours, fed). Overall, a high-fat meal increased the average Cmax of the methylphenidate ER liquid suspension of the invention by about 28% and the AUC by about 19%.

Example 8

Clinical Studies

Figure 5:
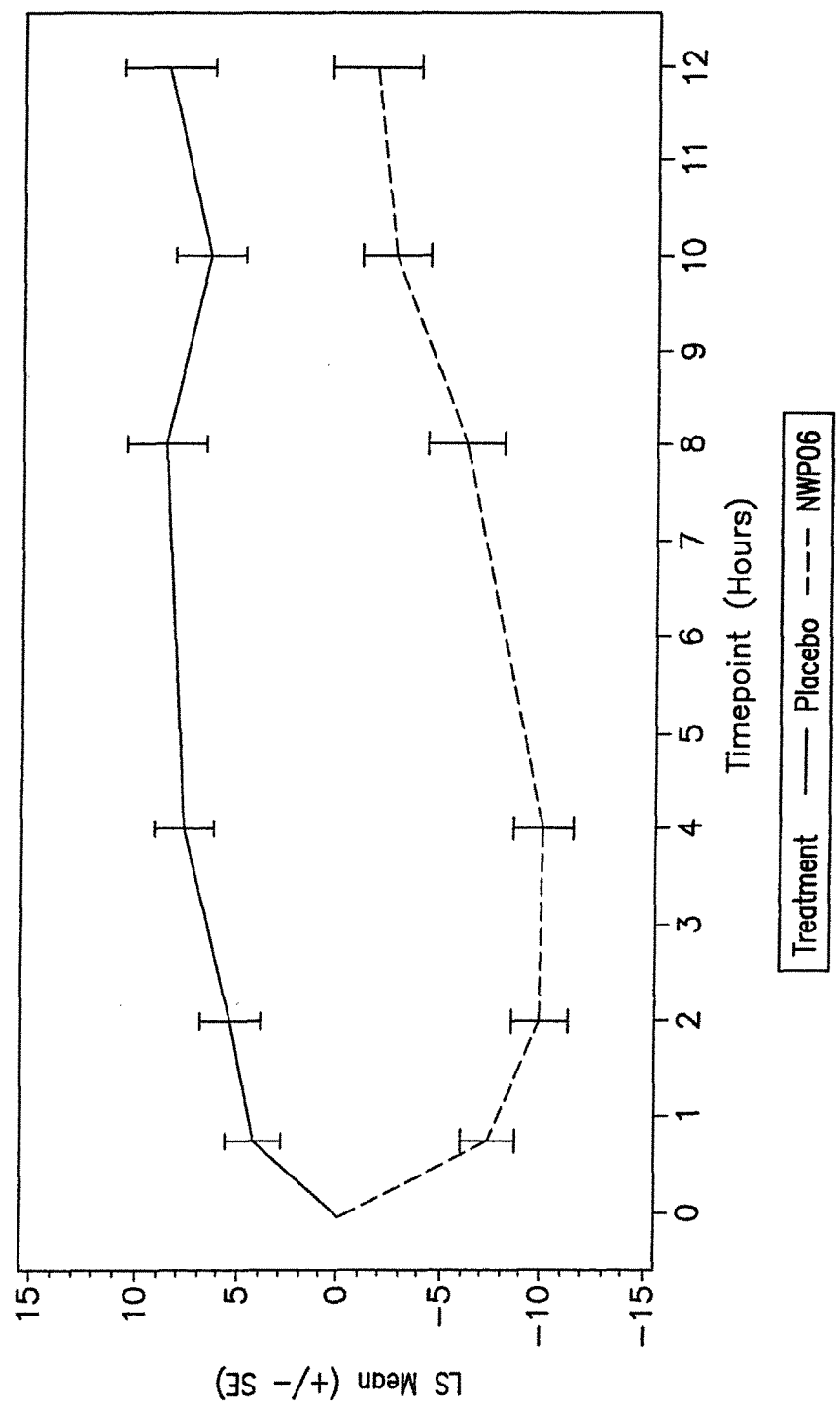
FIG. 5 illustrates the results of the study of Example 8, showing the change from baseline in the attention and behavior of the subjects in a laboratory classroom using the Swanson, Kotin, Agler, M-Flynn, and Pelham (SKAMP) rating scale. This is charted as the SKAMP-Combined Score.

The efficacy of the methylphenidate ER liquid suspension product prepared as described in Example 1 was evaluated in a randomized, double-blind, placebo-controlled, crossover, multicenter, laboratory classroom study conducted in 45 pediatric patients (ages 6 to 12 years) with ADHD. There was an open-label dose optimization period (4 to 6 weeks) with an initial 20 mg dose of MPH ER liquid suspension once daily in the morning. The dose could be titrated weekly in increments of 10 or 20 mg until an optimal dose or maximum dose of 60 mg/day was reached. Subjects then entered a 2-week randomized, double-blind, crossover treatment of the individually optimized dose of the tested MPH ER suspension or placebo. At the end of each week, schoolteachers and raters evaluated the attention and behavior of the subjects in a laboratory classroom using the Swanson, Kotin, Agler, M-Flynn, and Pelham (SKAMP) rating scale. Results of the study are summarized in FIG. 5. SKAMP scores were statistically significantly lower (improved) during treatment with the MPH ER suspension of the invention as compared to placebo. The onset of efficacy was determined to be 0.75 hours post-dose and efficacy was maintained throughout the entire 12-hour period.

All patents, patent publications, and other publications listed in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A methylphenidate aqueous extended release oral suspension comprising (1) an immediate release methylphenidate component, (2) a sustained release methylphenidate component comprising a water-insoluble, water-permeable, pH-independent, barrier coated methylphenidate-ion exchange resin complex, and (3) water,
wherein said suspension has a pH of about 3.5 to about 5 and said suspension provides a single mean average plasma concentration peak for methylphenidate and a therapeutically effective plasma profile for methylphenidate for about 12 hours.

2. The methylphenidate aqueous extended release oral suspension according to claim 1, wherein said suspension has a pH in the range of about 4 to about 4.5.

3. The suspension according to claim 1, wherein the barrier coating is selected from the group consisting of: (a) a cured water-permeable, high tensile strength, water insoluble, pH-independent barrier coating comprising a polyvinylacetate polymer and a plasticizer, (b) a barrier coating comprising an solvent-based ethylcellulose; and (c) a pH-independent acrylate based barrier coating comprising a methyl methyacrylate polymer or co-polymer.

4. The suspension according to claim 3, wherein the acrylate based barrier coating comprises a poly(ethyl acrylate-co-methyl methacrylate-co-trimethylammonoethyl methacrylate chloride) polymer system.

5. The suspension according to claim 1, wherein the immediate release methylphenidate component is an uncoated methylphenidate-ion exchange resin complex, optionally in combination with a hydrophilic or hydrophobic polymeric matrix forming component.

6. The suspension according to claim 1, wherein the suspension has a pharmacokinetic profile in which the single mean plasma concentration peak for d-methylphenidate has an area under the curve $(AUC)_{0-\infty}$ of about 114 ng-hr/mL to about 180 ng-hr/mL, $C_{max}$ of about 11 ng/mL to about 17 ng/mL, $T_{max}$ of about 4 hours to about 5.25 hours and $T_{1/2}$ of about 5 hours to about 7 hours following a single oral administration of an aqueous suspension at a dose equivalent to 60 mg racemic methylphenidate HCl in adults.

7. The methylphenidate aqueous extended release oral suspension according to claim 6 wherein the pharmacokinetic profile of d-methylphenidate has an $AUC_{0-\infty}$ of about 143.65 ng-hr/mL, $C_{max}$ of about 13.61 ng/mL, $T_{max}$ of about 5 hours and $T_{1/2}$ of about 5.65 hours following a single oral administration of an aqueous suspension at a dose equivalent to 60 mg racemic methylphenidate HCl in adults.

8. The suspension according to claim 1 wherein the suspension has a pharmacokinetic profile in which the single mean plasma concentration peak for methylphenidate has an area under the curve $(AUC)_{0-\infty}$ of about 137.2 to about 214.4 ng-hr/mL, a $C_{max}$ of about 13.6 to about 21.3 ng/mL, and $T_{max}$ of about 3 to about 5 hours, following a single oral administration of an aqueous suspension at a dose equivalent to 72 mg racemic methylphenidate HCl in adults.

9. The methylphenidate aqueous extended release oral suspension according to claim 8 wherein said suspension has a pharmacokinetic profile in which methylphenidate has an $AUC_{0-\infty}$ of about 171.5 ng-hr/mL, a $C_{max}$ of about 17.0 ng/mL, and a $T_{max}$ of about 3.77 hours following a single oral administration of an aqueous suspension at a dose equivalent to 72 mg racemic methylphenidate HCl in adults.

10. The suspension according to claim 1, wherein the methylphenidate ion exchange resin complex is in a matrix with about 5 to about 20% by weight of a hydrophilic or hydrophobic polymeric matrix forming component, based on the weight of the uncoated methylphenidate-ion exchange resin complex-matrix.

11. The suspension according to claim 10, wherein the polymeric matrix forming component is a hydrophilic polymer comprising polyvinylpyrrolidone.

12. The suspension according to claim 10, wherein the polymeric matrix forming component is a hydrophobic polymer comprising polyvinylacetate.

13. The suspension according to claim 1, wherein said suspension contains at least about 80% of water by weight based on the total weight of the suspension.

14. The suspension according to claim 1, wherein said methylphenidate in the immediate release and/or sustained release component is independently selected from the group consisting of racemic methylphenidate and dexmethylphenidate.

15. The suspension according to claim 1, wherein the barrier coat comprises about 20% to about 45% by weight of the coated methylphenidate-ion exchange resin complex-matrix.

16. The suspension according to claim 1, wherein the suspension contains about 10 to about 30 parts by weight of methylphenidate as provided in the immediate release component and to about 70 to about 90 parts by weight of sustained release methylphenidate, based upon the total weight of methylphenidate in the suspension.

17. The suspension according to claim 1, further comprising a buffering agent selected from the group consisting of one or more of a pharmaceutically acceptable acid selected from the group consisting of citric acid, ascorbic acid, acetic acid, tartaric acid, phosphoric acid, a pharmaceutically acceptable salt of citric acid, ascorbic acid, acetic acid, tartaric acid, phosphoric acid, or a mixture of said pharmaceutically acceptable acid or salt, and mixtures thereof.

18. The suspension according to claim 17, wherein the buffering agent is a mixture of sodium citrate and anhydrous citric acid.

19. A method for treating a patient having a condition susceptible to treatment with methylphenidate, the method comprising administering to the patient a methylphenidate aqueous extended release oral suspension of claim 1, wherein said suspension provides a therapeutically effective amount of methylphenidate within 45 minutes after administering of said suspension and a single average plasma concentration peak.

20. The method according to claim 19, wherein the suspension which has a pH from about 4 to about 4.5.

21. A methylphenidate extended release powder blend, said extended release powder blend comprising: (i) an immediate release methylphenidate component; (ii) a sustained release water-insoluble, water-permeable, pH-independent, diffusion barrier coating over a methylphenidate-ion exchange resin complex-matrix; (iii) a water soluble buffering agent which adjusts the pH of an aqueous suspension formed by admixing said extended release powder blend with water to a pH in the range of about 3.5 to about 5; and (iv) optional pharmaceutical excipients, wherein said powder blend provides a therapeutically effective profile of d-methylphenidate for about 12 hours and a single mean plasma concentration peak for d-methylphenidate.

22. The powder blend according to claim 21, wherein the barrier coating is selected from the group consisting of: (a) a cured water-permeable, high tensile strength, water insoluble, barrier coating comprising a polyvinylacetate polymer and a plasticizer; (b) a barrier coating comprising a solvent-based ethylcellulose; and (c) a poly(ethyl acrylate-co-methyl methacrylate-co-trimethylammoniumethyl-methacrylate chloride) polymer.

23. The powder blend according to claim 21, wherein said methylphenidate extended release powder blend further comprises water-soluble diluent granules which contain the buffering agent.

24. The powder blend according to claim 23, wherein the diluent granules further comprise one or more of a surfactant, a sweetener, and a preservative.

25. The powder blend according to claim 24, wherein the surfactant in the diluent granules comprises a poloxamer.

26. The powder blend according to claim 21, wherein said buffering agent is selected from the group consisting of one or more of a pharmaceutically acceptable acid selected from the group consisting of citric acid, ascorbic acid, acetic acid, tartaric acid, phosphoric acid, a pharmaceutically acceptable salt of citric acid, ascorbic acid, acetic acid, tartaric acid, phosphoric acid, or a mixture of said pharmaceutically acceptable acid or salt.

27. A tablet or capsule comprising the powder blend according to claim 21.

28. The methylphenidate aqueous extended release oral suspension according to claim 1 which has a stable shelf-life under ambient conditions over a period of at least about four months at room temperature.

29. The methylphenidate aqueous extended release oral suspension according to claim 28, which has less than about 5% loss in potency over a period of at least about 4 months of storage at room temperature.

30. The methylphenidate aqueous extended release oral suspension according to claim 29, which has less than about 3% loss in potency over a period of at least about 4 months of storage at room temperature.

* * * * *